US009682124B2

(12) United States Patent
Potter et al.

(10) Patent No.: US 9,682,124 B2
(45) Date of Patent: Jun. 20, 2017

(54) METHODS OF TREATING COGNITIVE IMPAIRMENT

(71) Applicants: Huntington Potter, Tampa, FL (US); Gary W. Arendash, Prescott, AZ (US); Steven Bennett, Jupiter, FL (US); Timothy Boyd, Seffner, FL (US)

(72) Inventors: Huntington Potter, Tampa, FL (US); Gary W. Arendash, Prescott, AZ (US); Steven Bennett, Jupiter, FL (US); Timothy Boyd, Seffner, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/145,303

(22) Filed: Dec. 31, 2013

(65) Prior Publication Data
US 2014/0255337 A1  Sep. 11, 2014

Related U.S. Application Data

(63) Continuation of application No. 13/057,387, filed as application No. PCT/US2009/052742 on Aug. 4, 2009, now abandoned.

(60) Provisional application No. 61/086,351, filed on Aug. 5, 2008.

(51) Int. Cl.
*A61K 38/00* (2006.01)
*A01N 37/18* (2006.01)
*A61K 38/18* (2006.01)
*A61K 38/17* (2006.01)
*A61K 38/19* (2006.01)

(52) U.S. Cl.
CPC ........ *A61K 38/193* (2013.01); *A61K 38/1709* (2013.01); *A61K 38/1816* (2013.01)

(58) Field of Classification Search
None
See application file for complete search history.

(56) References Cited

U.S. PATENT DOCUMENTS

| 4,559,157 | A | 12/1985 | Smith et al. |
| 4,608,392 | A | 8/1986 | Jacquet et al. |
| 4,820,508 | A | 4/1989 | Wortzman |
| 4,938,949 | A | 7/1990 | Borch et al. |
| 4,992,478 | A | 2/1991 | Geria |
| 5,034,322 | A | 7/1991 | Rogers et al. |
| 5,106,739 | A | 4/1992 | Comai et al. |
| 5,167,649 | A | 12/1992 | Zook |
| 5,625,136 | A | 4/1997 | Koziel et al. |
| 6,960,648 | B2 | 11/2005 | Bonny |
| 8,071,543 | B2 | 12/2011 | Schaebitz et al. |
| 8,398,972 | B2 | 3/2013 | Bebbington et al. |
| 2002/0035243 | A1 | 3/2002 | Imfeld et al. |
| 2002/0120100 | A1 | 8/2002 | Bonny |
| 2003/0032594 | A1 | 2/2003 | Bonny |
| 2004/0006780 | A1 | 1/2004 | Gerber et al. |
| 2006/0275294 | A1 | 12/2006 | Omoigui |
| 2008/0014193 | A1 | 1/2008 | Brines et al. |
| 2008/0318871 | A1 | 12/2008 | Khan et al. |

FOREIGN PATENT DOCUMENTS

| JP | 04198134 | 7/1992 |
| JP | 08-113535 | 5/1996 |
| KR | 10-2005-0019732 | 3/2005 |
| WO | WO 2006/055260 | 5/2006 |
| WO | WO 2009/029508 | 3/2009 |

OTHER PUBLICATIONS

Akiyama et al., "Inflammation and Alzheimer's disease", *Neurobiology of Aging*, May/Jun. 2000, vol. 21, No. 3, pp. 383-421.
Altschul et al., "Basic local alignment search tool", *Journal of Molecular Biology*, Oct. 1990, vol. 215, No. 3, pp. 403-410.
Altschul et al., "Gapped BLAST and PSI-BLAST: a new generation of protein database search programs", *Nucleic Acids Research*, Sep. 1997, vol. 25, No. 17, pp. 3389-3402.
Arendash et al., "Progressive, age-related behavioral impairments in transgenic mice carrying both mutant amyloid precursor protein and presenilin-1 transgenes", *Brain Research*, Feb. 2001, vol. 891, Nos. 1-2, pp. 42-53. Arendash et al., "A diet high in omega-3 fatty acids does not improve or protect cognitive performance in Alzheimer's transgenic mice", *Neuroscience*, Oct. 2007, vol. 149, No. 2, pp. 286-302.
Beltz et al., "Isolation of multigene families and determination of homologies by filter hybridization methods", *Methods in Enzymology*, R. Wu, L. Grossman and K. Moldave [eds.] Academic Press, New York, 1983, vol. 100, pp. 266-285.
Boissonneault et al., "Powerful beneficial effects of macrophage colony-stimulating factor on b-amyloid deposition and cognitive impairment in Alzheimer's disease", *Brain*, Apr. 2009, vol. 132, No. 4, pp. 1078-1092.
Bundgaard, "(C) Means to enhance penetration: (1) Prodrugs as a means to improve the delivery of peptide drugs", *Advanced Drug Delivery Reviews*, Jan./Feb. 1992, vol. 8, No. 1, pp. 1-38.

(Continued)

*Primary Examiner* — Olga N Chernyshev
(74) *Attorney, Agent, or Firm* — Saliwanchik Lloyd & Eisenschenk

(57) ABSTRACT

The subject invention concerns materials and methods for treating a person or animal having cognitive impairment. In one embodiment, the method comprises administering an effective amount of one or more inflammatory mediator(s), for example, fms-related tyrosine kinase 3 (Flt3) ligand, interleukin-6 (IL-6), macrophage migration inhibitory factor (MIF), interleukin-1 (IL-1), interleukin-3 (IL-3), erythropoietin (EPO), vascular endothelial growth factor A (VEGF-A), hypoxia-inducible transcription factor (HIF-1alpha), insulin like growth factor-1 (IGF-1), tumor necrosis factor (TNF), granulocyte colony-stimulating factor (G-CSF), granulocyte/macrophage colony-stimulating factor (GM-CSF), macrophage colony-stimulating factor (M-CSF), Stem Cell Factor (SCF), Darbepoetin (ARANESP), and metalloproteinases, to an animal or person in need of treatment.

15 Claims, 21 Drawing Sheets

(56) References Cited

OTHER PUBLICATIONS

Cadman et al., "β-amyloid peptides initiate the complement cascade without producing a comparable effect on the terminal pathway in vitro", *Experimental Neurology*, Aug. 1997, vol. 146. No. 2, pp. 388-394.
Cox et al., "Both Th1 and TH17 are immunopathogenic but differ in other key biological activities", *The Journal of Immunology*, Jun. 2008, vol. 180, No. 11, pp. 7414-7422.
Czygier et al., "Stem cell factor (SCF) in the plasma and phagocytic functions of granulocytes in breast cancer patients", *Przegl. Lek.*, 2007, vol. 64, No. 12, abstract.
De Boer et al., "The tac promoter: A functional hybrid derived from the *trp* and *lac* promoters", *PNAS: Proceedings of the National Academy of Sciences*, Jan. 1983, vol. 80, No. 1, pp. 21-25.
El Khoury et al., "Ccr2 deficiency impairs microglial accumulation and accelerates progression of Alzheimer-like disease", *Nature Medicine*, Apr. 2007, vol. 13, No. 4, pp. 432-438.
Ethell et al., "Abeta-specific T-cells reverse cognitive decline and synaptic loss in Alzheimer's mice", *Neurobiolgy of Disease*, Aug. 2006, vol. 23, No. 2, pp. 351-361.
Felgner et al., "Lipofection: a highly efficient, lipid-mediated DNA-transfection procedure", *Proceedings of the National Academy of Sciences of the United States of America*, Nov. 1987, vol. 84, No. 21, pp. 7413-7417.
Fisher, "Erythropoietin: physiology and pharmacology update", *Experimental Biology and Medicine*, Jan. 2003, vol. 228, No. 1, pp. 1-14.
Götz et al., "Formation of neurofibrillary tangles in P301l tau transgenic mice induced by Abeta 42 fibrils", *Science*, Aug. 2001, vol. 293, No. 5534, pp. 1491-1495.
Griffin et al., "Brain interleukin 1 and S-100 immunoreactivity are elevated in Down syndrome and Alzheimer disease", *Proceedings of the National Academy of Sciences of the United States of America*, Oct. 1989, vol. 86, No. 19, pp. 7611-7615.
Helmy et al., CRIg: A macrophage complement receptor required for phagocytosis of circulating pathogens, *Cell*, Mar. 2006, vol. 124, No. 5, pp. 915-927.
Hickman et al., "Microglial dysfunction and defective beta-amyloid clearance pathways in aging Alzheimer's disease mice", *The Journal of Neuroscience*, Aug. 2008, vol. 28, No. 33, pp. 8354-8360.
Humpel et al., "Cerebrovascular damage as a cause for Alzheimer's disease", *Current Neurovascular Reasearch*, Oct. 2005, vol. 2, No. 4, pp. 341-347.
Kakeya et al., "Studies on prodrugs of cephalosporins. I. [1)] Synthesis and biological properties of glycyloxybenzoyloxymethyl and glycylaminobenzoyloxymethyl esters of 7β-[2-(2-Aminothiazol-4-yl)-(Z)-2-methoxyiminoacetamido]-3-methyl-3-cephem-4-carboxylic acid", *Chemical and Pharmaceutical Bulletin*, 1984, vol. 32, No. 2, pp. 692-698.
Karlin et al., "Methods for assessing the statistical significance of molecular sequence features by using general scoring schemes", *PNAS: Proceedings of the National Academy of Sciences*, Mar. 1990, vol. 87, No. 6, pp. 2264-2268.
Karlin et al, "Applications and statistics for multiple high-scoring segments in molecular sequences", *PNAS: Proceedings of the National Academy of Sciences*, Jun. 1993, vol. 90, No. 12, pp. 5873-5877.
Kirma et al., "Overexpression of the colony-stimulating factor (CSF-1) and/or its receptor c-fms in mammary glands of transgenic mice results in hyperplasia and tumor formation", *Cancer Research*, Jun. 2004, vol. 64, pp. 4162-4170.
Koenigsknecht-Talboo et al., "Rapid microglial response around amyloid pathology following systemic anti-Aβ antibody administration in PDAPP mice", Journal of Neuroscience, Dec. 2008, vol. 28, No. 52, pp. 14156-14164.
Bundgaard, H. "Design and Applications of Prodrugs" in *A Textbook of Drug Design and Development*, Krogsgaard-Larsen et al., Eds., 1991, Chapter 5, pp. 113-191.

Krüger et al., "The hematopoietic factor GM-CSF (Granulocyte-macrophage colony-stimulating factor) promotes neuronal differentiation of adult neural stem cells in vitro", *BMC Neuroscience*, 2007, vol. 8, No. 88, 7 pages.
Leizer et al., "Cytokine regulation of colony-stimulating factor production in cultured human synovial fibroblasts: I. Induction of GM-CSF and G-CSF production by interleukin-1 and tumor necrosis factor", *Blood*, Nov. 1990, vol. 76, No. 10, pp. 1989-1996.
Loewenstein et al., "Semantic interference deficits and the detection of mild Alzheimer's disease and mild cognitive impairment without dementia", *Journal of the International Neuropsychological Society*, Jan. 2004, vol. 10, No. 1, pp. 91-100.
Ma et al., "Alzheimer Aβ neurotoxicity: Promotion by antichymotrypsin, ApoE4; inhibition by aβ-related peptides", *Neurobiology of Aging*, Sep./Oct. 1996, vol. 17, No. 5, pp. 773-780.
Malm et al., "Bone-marrow-derived cells contribute to the recruitment of microglial cells in response to b-amyloid deposition in APP/PS1 double transgenic Alzheimer mice", *Neurobiology of Disease*, Feb. 2005, vol. 18, No. 1, pp. 134-142.
Martin et al., "Cognitive Function Over Time in the Alzheimer's Disease Antiinflammatory Prevention Trial (ADAPT): Results of a Randomized, Controlled Trial of Naproxen and Celecoxib", *Archives of Neurology*, Jul. 2008, vol. 65, No. 7, pp. 896-905.
McGeer et al., "Inflammation, anti-inflammatory agents and Alzheimer disease: The last 12 years", *Journal of Alzheimer's Disease*, 2006, vol. 9, pp. 271-276.
Meyer-Luehmann, "Rapid appearance and local toxicity of amyloid-β plaques in a mouse model of Alzheimer's disease", *Nature*, Feb. 2008, vol. 451, pp. 720-724.
Nakamura et al., "High serum and synovial fluid granulocyte colony stimulating factor (GCSF) concentrations in patients with rheumatoid arthritis", *Clinical and Experimental Rheumatology*, 2000, vol. 18, No. 6, pp. 713-718.
Nielsen et al., "Glycolamide esters as biolabile prodrugs of carboxylic acid agents: Synthesis, stability, bioconversion and physicochemical properties", *Journal of Pharmaceutical Sciences*, Apr. 1988, vol. 77, No. 4, pp. 285-298.
Nilsson et al., "Cognitive impairment in PDAPP mice depends on ApoE and ACT-catalyzed amyloid formation", *Neurobiology of Aging*, Oct. 2004, vol. 25, No. 9, pp. 1153-1167.
Notari, R.E. "Theory and Practice of Prodrug Kinetics" in Methods in enzymology, Widder et al., Eds., Academic Press, 1985, vol. 42, pp. 309-396.
Padmanabhan et al., "Alphal-antichymotrypsin, an inflammatory protein overexpressed in Alzheimer's disease brain, induces tau phosphorylation in neurons", *Brain*, Nov. 2006, vol. 129, No. 11, pp. 3020-3034.
Parsonage et al., "Prolonged, granulocyte-macrophage colony-stimulating factor-dependent, neutrophil survival following rheumatoid synovial fibroblast activation by IL-17 and TNFalpha", *Arthritis Research and Therapy*, Apr. 2008, vol. 10, No. 2, 12 pages.
Potter et al., "The inflammation-induced pathological chaperones ACT and apo-E are necessary catalysts of Alzheimer amyloid formation", *Neurobiology of Aging*, Nov./Dec. 2001, vol. 22, No. 6, pp. 923-930.
Rapoport et al., "Tau is essential to beta-amyloid-induced neurotoxicity", *Proceedings of the National Academy of Sciences of the United States of America*, Apr. 2002, vol. 99, No. 9, pp. 6364-6369.
Rhodin et al., "Animal model of Alzheimer-like vascular pathology and inflammatory reaction", *Annals of the New York Academy of Sciences*, Apr. 2000, vol. 903, pp. 345-352.
Ritchie et al., "The dementias", *Lancet*, Nov. 2002, vol. 360, No. 9347, pp. 1759-1766.
Rogers et al., "Peripheral clearance of amyloid beta peptide by complement C3-dependent adherence to erythrocytes", *Neurobiology of Aging*, Dec. 2006, vol. 27, No. 12, pp. 1733-1739.
Sanchez-Ramos et al., "Granulocyte colony stimulating factor decreases brain amyloid burden and reverses cognitive impairment in Alzheimer's mice", *Neuroscience*, Sep. 2009, vol. 163, No. 1, pp. 55-72.

(56) References Cited

OTHER PUBLICATIONS

Schellekens et al., "The diagnostic properties of rheumatoid arthritis antibodies recognizing a cyclic citrullinated peptide", *Arthritis and Rheumatism*, Jan. 2000, vol. 43, No. 1, pp. 155-163.

Scheuner et al., "Secreted amyloid β-protein similar to that in the senile plaques of Alzheimer's disease is increased in vivo by the presenilin 1 and 2 and APP mutations linked to familial Alzheimer's disease", *Nature Medicine*, Aug. 1996, vol. 2, No. 8, pp. 864-870.

Seitz et al., "Constitutive mRNA and protein production of macrophage colony-stimulating factor but not of other cytokines by synovial fibroblasts from rheumatoid arthritis and osteoarthritis patients", *British Journal of Rheumatology*, 1994, vol. 33, pp. 613-619.

Simard et al., "Bone marrow stem cells have the ability to populate the entire central nervous system into fully differentiated parenchymal microglia", *The FASEB Journal*, Jun. 2005, vol. 18, 9 pages.

Simard et al., "Bone marrow-derived microglia play a critical role in restricting senile plaque formation in Alzheimer's disease", *Neuron*, Feb. 2006, vol. 49, No. 4, pp. 489-502.

Streit et al., "Dystrophic (senescent) rather than activated microglial cells are associated with tau pathology and likely precede neurodegeneration in Alzheimer's disease", *Acta Neuropathologica*, Oct. 2009, vol. 118, No. 4, pp. 475-485.

Szekanecz et al., "Macrophages and their products in rheumatoid arthritis", *Current Opinion in Rheumatology*, May 2007, vol. 19, No. 3, pp. 289-295.

Van Der Voort et al., "Elevated CXCL16 expression by synovial macrophages recruits memory T cells into rheumatoid joints", *Arthritis and Rheumatism*, May 2005, vol. 52, No. 5, pp. 1381-1391.

Wisniewski et al., "Acceleration of Alzheimer's fibril formation by apolipoprotein E in vitro", *American Journal of Pathology*, Nov. 1994, vol. 145, No. 5, pp. 1030-1035.

Wyss-Coray et al., "Prominent neurodegeneration and increased plaque formation in complement-inhibited Alzheimer's mice", *Neurobiology*, Aug. 2002, vol. 99, No. 16, pp. 10837-10842.

Wyss-Coray, "Inflammation in Alzheimer disease: driving force, bystander or beneficial response?", *Nature Medicine*, Sep. 2006, vol. 12, No. 9, pp. 1005-1015.

Xu et al., "Systemic induction of a potato pin2 promoter by wounding, methyl jasmonate, and abscisic in transgenic rice plants", *Plant Molecular Biology*, Jul. 1993, vol. 22, No. 4, pp. 573-588.

Dong, J. et al., "Flt-3 Ligand—A Potent Dendritic Cell Stimulator and Novel Antitumor Agent," *Cancer Biology & Therapy*, Sep./Oct. 2002, pp. 486-489, vol. 1, No. 5.

Jacobs et al. "Changes in cognitive functioning in the year after hematopoietic stem cell transplantation" *Cancer*, Oct. 1, 2007, 110(7):1560-1567.

Boyd, T.D. et al. "GM-CSF upregulated in rheumatoid arthritis reverses cognitive impairment and amyloidosis in Alzheimer mice" *J. Alzheimer's Dis.*, 2010, 21:507-518.

Franzen, R. "Nervous system injury: focus on the inflammatory cytokine 'granulocyte-macrophage colony stimulating factor'" *Neuroscience Letters*, 2004, 361:76-78.

Kim, H-D. et al. "Induction of anti-inflammatory immune response by an adenovirus vector encoding 11 tandem repeats of Aβ1-6: Toward safer and effective vaccines against Alzheimer's disease" *Biochemical and Biophysical Research Communications*, 2005, 336:84-92.

Kim, H-D. et al. "Induction of a Th2 immune response by co-administration of recombinant adenovirus vectors encoding amyloid β-protein and GM-CSF" *Vaccine*, 2005, 23:2977-2986.

Volmar, C-L. et al. "The granulocyte macrophage colony stimulating factor (GM-CSF) regulates amyloid β (Aβ) production" *Cytokine*, 2008, 42(3):336-344.

Dasilva, K. et al. "Immunization with amyloid-β using GM-CSF and IL-4 reduces amyloid burden and alters plaque morphology" *Neurobiology of Disease*, 2006, 23:433-444.

Kim, H-D. et al. "Immunization of Alzheimer model mice with adenovirus vectors encoding amyloid β-protein and GM-CSF reduces amyloid load in the brain" *Neurosci. Letters*, 2004, 370:218-223.

Tsai K-J et al. "G-CSF rescues the memory impairment of animal models of Alzheimer's disease" *The Journal of Experimental Medicine*, 2007, 204(6):1273-1280.

Abbas, N et al. "Up-regulation of the inflammatory cytokines IFN-gamma and IL-12 and down-regulation of IL-4 in cerebral cortex regions of APP(SWE) transgenic mice" *J. Neuroimmunol.*, 2002, 126:50-57.

Apelt, J et al. "Beta-amyloid-induced glial expression of both pro- and anti-inflammatory cytokines in cerebral cortex of aged transgenic Tg2576 mice with Alzheimer plaque pathology" *Brain Res.*, Mar. 2001, 894(1):21-30.

Be'eri, H et al. "The cytokine network of wallerian degeneration: IL-10 and GM-CSF" *Eur. J. Neurosci.*, Aug. 1998, 10(8):2707-2713.

Blusztajn, JK et al. "Phosphatidylcholine as a precursor of choline for acetylcholine synthesis" *J. Neural Transm. Suppl.*, 1987, 24:247-259; abstract only.

Blusztajn, JK et al. "Synthesis of acetylcholine from choline derived from phosphatidylcholine in a human neuronal cell line" *Proc. Nat'l Acad. Sci. USA*, Aug. 1987, 84(15):5474-5477.

Frautschy, SA et al. "Microglial response to amyloid plaques in APPsw transgenic mice" *Am. J. Pathol.*, Jan. 1998, 152(1):307-317.

Giulian, D et al. "The impact of microglia-derived cytokines upon gliosis in the CNS" *Developmental Neuroscience*, 1994, 16(3-4):128-136; abstract only.

Henze, C et al. "Proliferation of microglial cells induced by 1-methyl-4-phenylpyridinium in mesencephalic cultures results from an astrocyte-dependent mechanism: role of granulocyte macrophage colony-stimulating factor" *J. Neurochem.*, Nov. 2005, 95(4):1069-1077.

Jacobs, SR et al. "Changes in cognitive functioning in the year after hematopoietic stem cell transplantation" *Cancer*, Oct. 2007, 110(7):1560-1567.

Koguchi, K et al. "Microglial cell cycle-associated proteins control microglial proliferation in vivo and in vitro and are regulated by GM-CSF and density-dependent inhibition" *J. Neurosci. Res.*, Dec. 2003, 74(6):898-905.

Kreutzberg, GW "Microglia: a sensor for pathological events in the CNS" *Trends in Neurosciences*, 1996, 19(8):312-318.

Matsuoka, Y et al. "Fibrillar beta-amyloid evokes oxidative damage in a transgenic mouse model of Alzheimer's disease" *Neuroscience*, 2001, 104(3):609-613.

McGeer, EG et al. "Inflammatory processes in Alzheimer's disease" *Progress in Neuropsychopharmacology & Biological Psychiatry*, Aug. 2003, 27(5):741-749.

Mehlhorn, G et al. "Induction of cytokines in glial cells surrounding cortical beta-amyloid plaques in transgenic Tg2576 mice with Alzheimer pathology" *Int'l J. Devl. Neurosci.*, Jul.-Aug. 2000, 18:423-431.

Norton, WT et al. "Quantitative aspects of reactive gliosis: a review" *Neurochemical Res.*, 1992, 17(9):877-885.

Patel, NS et al. "Inflammatory cytokine levels correlate with amyloid load in transgenic mouse models of Alzheimer's disease" *J. Neuroinflammation*, Mar. 2005, 2(1):9.

Ponomarev, ED et al. "GM-CSF production by autoreactive T cells is required for the activation of microglial cells and the onset of experimental autoimmune encephalomyelitis" *J. Immunol.*, Jan. 2007, 178(1):39-48.

Stalder, M et al. "Association of microglia with amyloid plaques in brains of APP23 transgenic mice" *Am. J. Pathol.*, Jun. 1999, 154(6):1673-1684.

Tabira, T et al. "Neurotrophic effect of hematopoietic cytokines on cholinergic and other neurons in vitro" *Int'l J. Devl. Neuroscience*, Jun.-Jul. 1995, 13(3-4):241-252.

(56) References Cited

OTHER PUBLICATIONS

Tarkowski, E et al. "Local and systemic GM-CSF increase in Alzheimer's disease and vascular dementia" *Acta Neurologica Scandinavica*, Mar. 2001, 103(3):166-174.

Ulus, IH et al., "Choline increases acetylcholine release and protects against the stimulation-induced decrease in phosphatide levels within membranes of rat corpus striatum" *Brain Res.*, Apr. 1989, 484(1-2):217-227.

Wegiel, J et al. "The role of microglial cells and astrocytes in fibrillar plaque evolution in transgenic $APP_{sw}$ mice" *Neurobiology of Aging*, Jan.-Feb. 2001, 22(1):49-61.

Yavin, E et al. "Phospholipid-derived choline intermediates and acetylcholine synthesis in mouse brain synaptosomes" *J. Neurosci. Res.*, Oct. 1989, 24(2):241-246; abstract only.

Zaheer, A et al. "A novel role of glia maturation factor: induction of granulocyte-macrophage colony-stimulating factor and pro-inflammatory cytokines" *J. Neurochem.*, Apr. 2007, 101(2):364-376, Epub Jan. 22, 2007.

Jack, CR et al. "Serial PIB and MRI in normal, mild cognitive impairment and Alzheimer's disease: implications for sequence of pathological events in Alzheimer's disease" *Brain*, May 2009, 132:1355-1365.

Arendash, G. et al. "Environmental enrichment improves cognition in aged Alzheimer's transgenic mice despite stable b-amyloid deposition" *NeuroReport*, Aug. 6, 2004, 15(11):1751-1754.

Costa, D. et al. "Enrichment improves cognition in AD mice by amyloid-related and unrelated mechanisms" *Neurobiol Aging*, 2007 (Epub: May 26, 2006), 28(6):831-844.

Schenk, D. et al. "Therapeutic approaches related to amyloid-β peptide and Alzheimer's disease" *J Med Chem.*, Oct. 13, 1995, 38(21):4141-4154.

Schenk, D. et al. "Immunization with amyloid-β attenuates Alzheimer-disease-like pathology in the PDAPP mouse" *Nature*, Jul. 8, 1999, 400:173-177.

Simmons, L. et al. "Secondary Structure of Amyloid β Peptide Correlates with Neurotoxic Activity In Vitro" *Mol Pharmacol.*, Mar. 1994, 45(3):373-379.

FIG. 7A
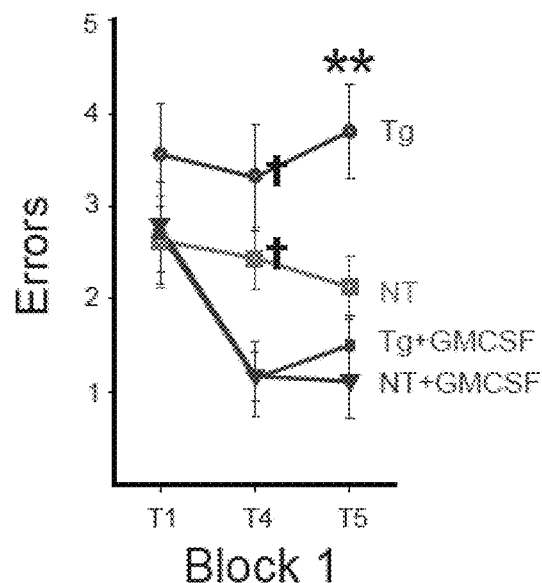
Block 1
FIG. 7B
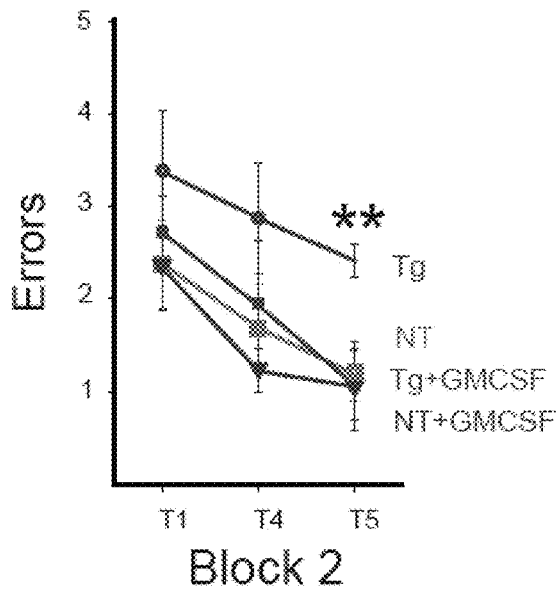
Block 2
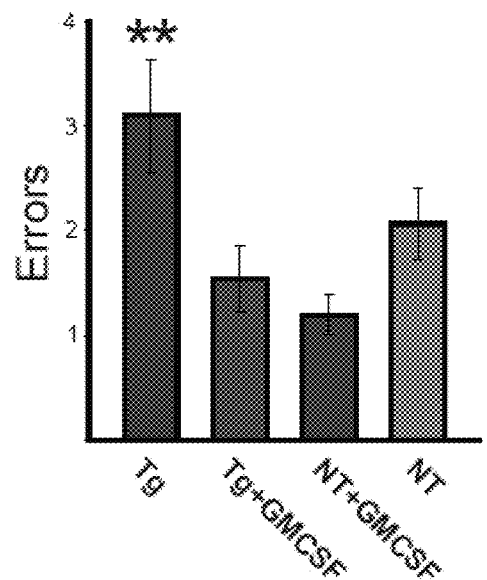
FIG. 7C
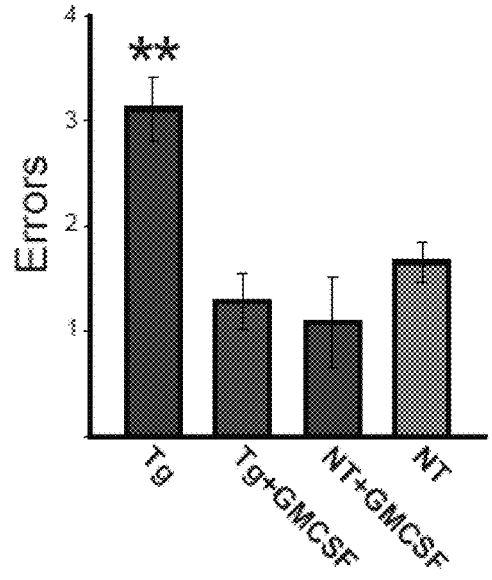
FIG. 7D

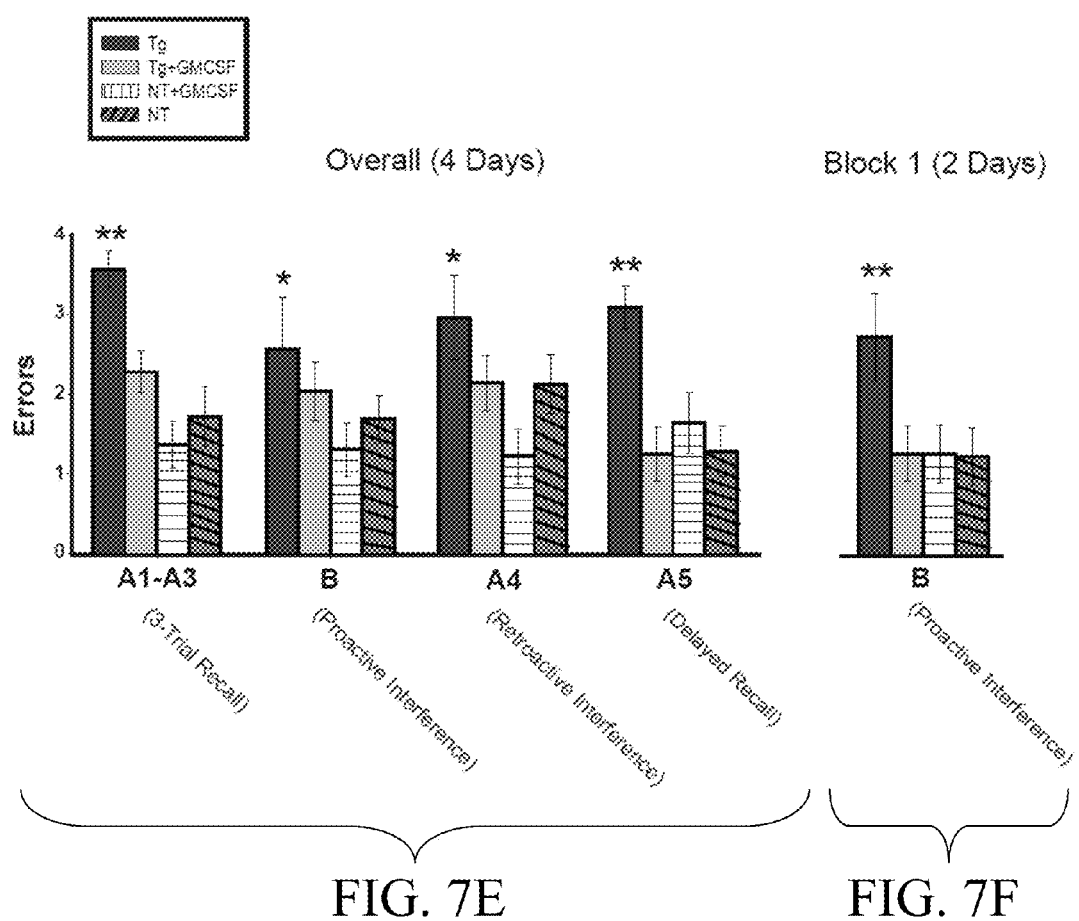

FIG. 8A
FIG. 8B
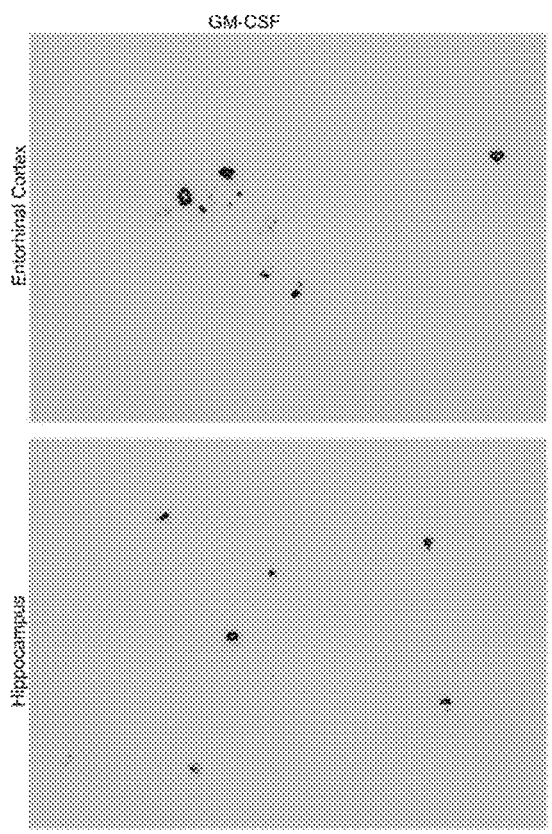
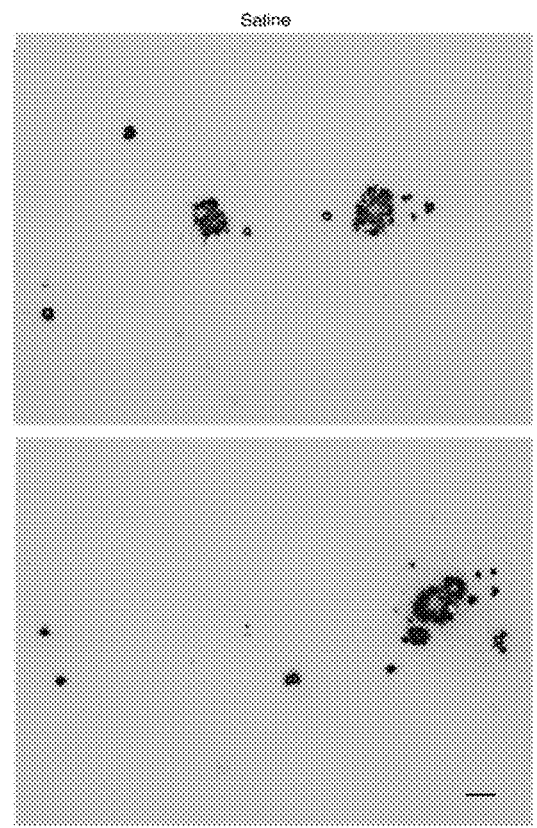
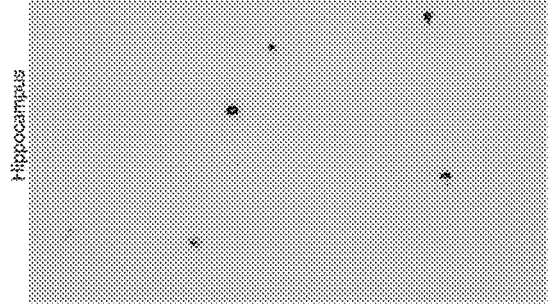
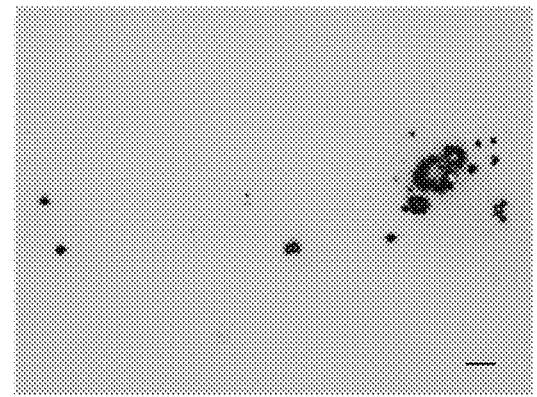
FIG. 8C
FIG. 8D

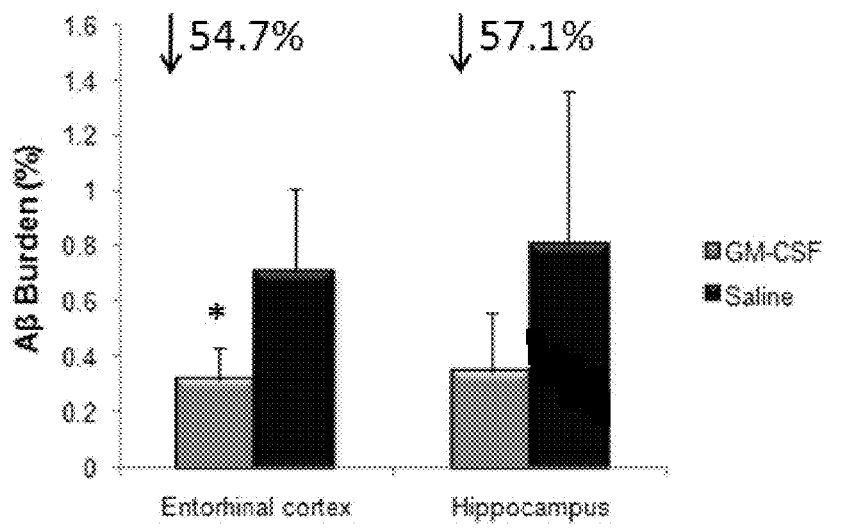
FIG. 8E
FIG. 9A  FIG. 9C
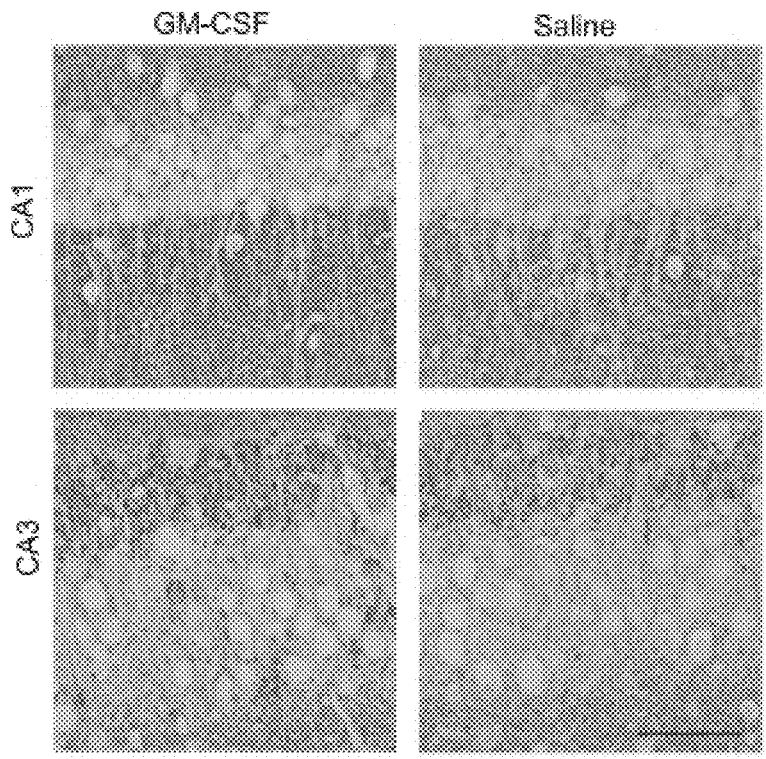
FIG. 9B  FIG. 9D

SEQUENCE LISTING

```
<160> NUMBER OF SEQ ID NOS: 1

<210> SEQ ID NO 1
<211> LENGTH: 144
<212> TYPE: PRT
<213> ORGANISM: Homo sapiens

<400> SEQUENCE: 1

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
        130                 135                 140
```

METHODS OF TREATING COGNITIVE IMPAIRMENT

CROSS-REFERENCE TO RELATED APPLICATIONS

The present application is a continuation of U.S. application Ser. No. 13/057,387, filed Feb. 3, 2011, which is the National Stage of International Application Number PCT/US2009/052742, filed Aug. 4, 2009, which claims the benefit of U.S. Provisional Application Ser. No. 61/086,351, filed Aug. 5, 2008, each of which is hereby incorporated by reference herein in its entirety, including any figures, tables, nucleic acid sequences, amino acid sequences, and drawings.

BACKGROUND OF THE INVENTION

Memory loss has long been recognized as a common accompaniment of aging. The inabilities to recall the name of a recent acquaintance or the contents of a short shopping list are familiar experiences for everyone, and this experience seems to become more common as we age.

Over the last few decades, the medical community has changed its view of memory loss in the elderly. These problems were viewed in the past as inevitable accompaniments of aging, often referred to as "senility" or "senior moments." More recently, physicians have shifted their view of memory loss, such that memory impairment of a certain degree is now considered pathological, and thus indicative of a disease process affecting the brain. The threshold most physicians use to make this judgment is that memory loss has progressed to such an extent that normal independent function is impossible; for instance, if one can no longer successfully manage one's own finances or provide for one's own basic needs. This degree of cognitive impairment has come to be referred to as dementia.

However, many older individuals may complain of memory problems, but still manage to independently accomplish all their customary tasks. Usually, their ability to function well is based on compensation for these difficulties, such as increased reliance on a calendar or on reminder notes, lists, etc. In some cases, these memory difficulties are a sign that worsening memory loss is on the horizon.

The syndrome of subjective memory problems has come to be commonly known as "Mild Cognitive Impairment" (MCI), although other terms have been used, including "Cognitive Impairment, Not Dementia" (CIND). The patient with MCI complains of difficulty with memory. Typically, the complaints include trouble remembering the names of people they met recently, trouble remembering the flow of a conversation, and an increased tendency to misplace things, or similar problems. In many cases, the individual will be quite aware of these difficulties and will compensate with increased reliance on notes and calendars. Most importantly, the diagnosis of MCI relies on the fact that the individual is able to perform all their usual activities successfully, without more assistance from others than they previously needed.

Several studies have examined the cognitive performance of patients with MCI. These have demonstrated that, in general, these patients perform relatively poorly on formal tests of memory, even when compared with other individuals in their age group. They also show mild difficulties in other areas of thinking, such as naming objects or people (coming up with the names of things) and complex planning tasks. These problems are similar, but less severe, than the neuropsychological findings associated with Alzheimer's disease. Careful questioning has also revealed that, in some cases, mild difficulties with daily activities, such as performing hobbies, are evident.

Several studies have demonstrated that memory complaints in the elderly are associated with a higher-than-normal risk of developing dementia in the future. Most commonly, the type of dementia that patients with MCI are at risk to develop is Alzheimer's disease, though other dementias, such as Vascular Dementia or Frontotemporal Dementia may occur as well. However, it is also clear that some patients with these complaints never develop dementia.

Certain features are associated with a higher likelihood of progression. These include confirmation of memory difficulties by a knowledgeable informant (such as a spouse, child, or close friend), poor performance on objective memory testing, and any changes in the ability to perform daily tasks, such as hobbies or finances, handling emergencies, or attending to one's personal hygiene.

One factor that had to be controlled for in many of these studies was depression, as many patients with depression also complain about their memory. Several studies have suggested that certain measurements of atrophy (shrinkage) or decreased metabolism on images of the brain (PET or MRI scans) increase the chances of developing dementia in the future.

Although these above factors increase the chances of going on to develop dementia, it is not possible currently to predict with certainty which patients with MCI will or will not go on to develop dementia. Thus, many of these measures, particularly the measurements from brain images, are still considered to be useful only for research.

One neurological disorder that is most widely known for its progressive loss of intellectual capacities is Alzheimer's disease (AD). Worldwide, about 20 million people suffer from Alzheimer's disease. AD is clinically characterized by the initial loss of memory, followed by disorientation, impairment of judgment and reasoning, which is commonly referred to as cognitive impairment, and ultimately by full dementia. AD patients finally lapse into a severely debilitated, immobile state between four and twelve years after onset of the disease.

The key pathological evidence for AD is the presence of extracellular amyloid plaques and intracellular tau tangles in the brain, which are associated with neuronal degeneration (Ritchie and Lovestone (2002)). The extracellular amyloid plaques are believed to result from an increase in the insoluble amyloid beta peptide 1-42 produced by the metabolism of amyloid-beta precursor protein (APP). Following $\beta$, $\gamma$ secretion, these amyloid beta 1-42 peptides form amyloid fibrils more readily than the amyloid beta 1-40 peptides, which are predominantly produced in healthy people. It appears that the amyloid beta peptide is on top of the neurotoxic cascade: experiments show that amyloid beta fibrils, when injected into the brains of P301 L tau transgenic mice, enhance the formation of neurofibrillary tangles (Götz et al. (2001)). In fact, a variety of amyloid beta peptides have been identified as amyloid beta peptides 1-42, 1-40, 1-39, 1-38, 1-37, which can be found in plaques and are often seen in cerebral spinal fluid.

The amyloid beta peptides are generated (or processed) from the membrane anchored APP, after cleavage by beta secretase and gamma secretase at position 671 and 711 or 713, respectively. In addition, high activity of beta secretase results in a shift of the cleavage at position 1 to position 11. Cleavage of amyloid-beta precursor protein by alpha secretase activity will generate A$\beta$ 1-17 and gamma secretase activity at 40 or 42 generates the non-pathological p3 peptide. Beta secretase was identified as the membrane anchored aspartyl protease BACE, while gamma secretase is a protein complex comprising presenilin 1 (PS1) or presenilin 2 (PS2), nicastrin, Anterior Pharynx Defective 1 (APH1) and Presenilin Enhancer 2 (PEN2). Of these proteins, the presenilins are widely thought to constitute the catalytic activity of the gamma secretase, while the other components play a role in the maturation and localization of the complex. The identity of the alpha secretase is still illustrious, although some results point towards the proteases ADAM 10 and TACE, which could have redundant functions.

A small fraction of AD cases (mostly early onset AD) are caused by autosomal dominant mutations in the genes encoding presenilin 1 and 2 (PS1; PS2) and the amyloid-beta precursor protein (APP), and it has been shown that mutations in APP, PS1 and PS2 alter the metabolism of amyloid-beta precursor protein leading to such increased levels of amyloid beta 1-42 produced in the brain. Although no mutations in PS1, PS2 and amyloid-beta precursor protein have been identified in late onset AD patients, the pathological characteristics are highly similar to the early onset AD patients. These increased levels of amyloid beta peptide could originate progressively with age from disturbed amyloid-beta precursor protein processing (e.g. high cholesterol levels enhance amyloid beta peptide production) or from decreased amyloid beta peptide catabolism. Therefore, it is generally accepted that AD in late onset AD patients is also caused by aberrant increased amyloid peptide levels in the brains. The level of these amyloid beta peptides, and more particularly amyloid-beta peptide 1-42, is increased in Alzheimer patients compared to the levels of these peptides in healthy persons.

BRIEF SUMMARY OF THE INVENTION

The present invention provides materials and methods for treating a person or animal having cognitive impairment wherein the method comprises administering an effective amount of an inflammatory mediator that is able to cross the blood brain barrier. In one embodiment, the inflammatory mediator provides for an increase in cognitive responses in the brain and/or exerting a neural protective effect. Inflammatory mediators contemplated within the scope of the present invention include, but are not limited to, fms-related tyrosine kinase 3 (Flt3) ligand, interleukin-6 (IL-6), macrophage migration inhibitory factor (MIF), interleukin-1 (IL-1), interleukin-3 (IL-3), erythropoietin (EPO), vascular endothelial growth factor A (VEGF-A), hypoxia-inducible transcription factor (HIF-1alpha), insulin like growth factor-1 (IGF-1), tumor necrosis factor (TNF), granulocyte colony-stimulating factor (G-CSF), granulocyte/macrophage colony-stimulating factor (GM-CSF), macrophage colony-stimulating factor (M-CSF), Stem Cell Factor (SCF), Darbepoetin (ARANESP), and metalloproteinases. In one embodiment, the inflammatory mediator is GM-CSF, or a functional fragment or variant thereof. In a specific embodiment, the cognitive impairment is caused by or results from Alzheimer's disease. In addition, it is also contemplated that compounds capable of inducing GM-CSF production in a mammal, which subsequently exert an increase in cognitive responses in the brain, can be used according to the subject invention. In one embodiment, the inflammatory mediator is administered or delivered to a non-neural cell or tissue of the human or animal.

The subject invention also concerns methods for decreasing or inhibiting the progression of cognitive impairment in a person or animal having memory problems associated with cognitive functions or related dementias, comprising administering an effective amount of an inflammatory mediator as described herein.

BRIEF DESCRIPTION OF THE DRAWINGS

FIG. 1 shows the diagram of the maze as one would look down on the device. FIG. 2 shows the device itself which is used for the behavioral testing of animals.

FIG. 6A shows intrahippocampal injection of GM-CSF (left hemisphere) and aCSF (right hemisphere). Representative coronal tissue cryosectioned at 14 µm and stained with MabTech α-Aβ/Alexa 546. Image is a montage of about 145 pictures taken at 10x. White spots indicate amyloid plaque immunolabelling (see FIGS. 13A-13D for representative montaged sections of all 4 mice). FIG. 6B: overall plaque reductions seen in all 4 plaque parameters measured, computated from 5 quantified sections per mouse (n=4 mice). Error bars are ±SEM. Statistical significance obtained by paired Students t-test with P values (Area: $P<1.11E-07$; Perimeter: $P<1.41E-06$; Feret Diameter: $P<2.36E-09$; Integrated Density: $P<1.11E-07$).

FIGS. 7A-7F show behavioral analysis following daily subcutaneous GM-CSF injections. FIGS. 7A-7D show standard Radial Arm Water Maze errors. Shows substantial impairment in Tg control mice (n=8) on working memory trials T4 and T5 compared to NT control mice (n=8) in individual blocks of testing (FIGS. 7A and 7B), and over all 4 days of testing (FIGS. 7C and 7D). GM-CSF-treated Tg mice (n=7) performed as well as or better than NT control mice on working memory trials T4 and T5 during individual blocks and over all. GM-CSF-treated NT mice (n=9) performed similarly to or slightly better than NT controls (Note significantly better performance of NT+GMCSF group vs. NT group for T4 of Block 1, FIG. 7A), although this effect was not significant overall. Statistical significance determined by one-way ANOVA (**$P<0.05$ or higher significance versus all other groups; † $P<0.05$ or higher significance versus Tg+GM-CSF and NT+GM-CSF). FIG. 7E shows cognitive Interference Task Overall (4 Days) Shows Tg control mice are impaired compared to NT mice on all four cognitive measures assessed. GM-CSF-treated Tg mice exhibited significantly better a-trial recall (A1-A3) and delayed recall (A5) compared to Tg controls and performed similarly to NT mice in all four cognitive measures. GM-CSF treatment of NT mice did not result in significantly better performance compared to NT controls, although trends for a beneficial GM-CSF effect in NT mice were evident overall. Statistical significance was determined by one-way ANOVA (*Tg significantly different from NT+GM-CSF, Tg significantly different from all other groups). FIG. 7F shows cognitive Interference Task. Proactive Interference testing (First 2 days). GM-CSF-treated Tg mice performed significantly better than Tg controls and equally to NT and GM-CSF-treated NT mice. Statistical significance determined by one-way ANOVA (P<0.05 or higher significance versus all other groups).

FIGS. 8A-8E show amyloid deposition in subcutaneous GM-CSF-injected mice. FIGS. 8A-8D are photomicrographs of coronal 5 µm paraffin-embedded sections immunolabelled with anti-Aβ antibody (clone 4G8). Pictures are representative of amyloid load closest to the mean of the GM-CSF- or saline-treated Tg groups. Scale bar=50 µm. FIG. 8E shows the percent of amyloid burden from the average of 5 sections per mouse of GM-CSF-treated (n=5) versus saline-treated (n=6). Statistical significance was determined by two-tailed homoscedastic Student's t-test: Entorhinal cortex (*P<0.026), and Hippocampus (P=0.12).

FIGS. 9A-9E shows synaptophysin immunostaining in subcutaneous GM-CSF-injected mice. FIGS. 9A-9D are photomicrographs of coronal 5 µm paraffin-embedded sections immunolabelled with anti-synaptophysin antibody. Pictures are representative of synaptophysin immunolabelling closest to the mean of the GM-CSF- or saline-treated groups. Scale bar=50 µm. FIG. 9E shows the percent of synaptophysin immunoreactivity from the average of 5 sections per mouse of GM-CSF-treated (n=5) versus saline-treated (n=6). Albeit numerically small, differences between the two groups were statistically significant by two-tailed homoscedastic Student's t-test: CA1(P<0.0013), CA3 (P<0.0023).

In FIG. 11A, the image is a montage of ~145 10× pictures and is representative of the effects seen from anterior hippocampus to posterior in all 4 M-CSF-injected mice. The M-CSF-injected hemispheres show no difference of amyloid deposition between hemispheres. FIG. 11B: This photo shows enlargement of the M-CSF-injected left hemisphere, as seen following saline perfusion. Note the small bump at the site of injection. FIG. 11C is an image showing cyst or tumor-like growth formed in the needle track at the site of M-CSF injection. Cryosectioned at 14 µm and stained with 6E10/Alexa 488 and Hoechst. Bright green staining is non-specific and not indicative of amyloid plaque. Picture taken at 20×.

FIGS. 13A-13C are from 14 µm frozen sections, and FIG. 13D is from a 5 µm paraffin-embedded section.

FIGS. 14A, 14A-1, 14B, 14B-1, 14C, 14C-1, 14D, 14D-1, 14E, 14E-1, 14F and 14F-1 show quantification of reduced amyloid deposition in GM-CSF-injected left hemispheres versus aCSF—injected contralateral right hemispheres. There were 5 sections per mouse quantified. Each montaged section contained over 140 10× pictures and of these, 15-25 pictures per hemisphere were selected to quantify. All pictures per section were taken at the same exposure on a Zeiss Imager.Z1 fluorescence microscope with a Zeiss Axiocam Mrm camera (Oberkochen, Germany) using Axiovision 4.7 software. Each figure shows total or average values from the 5 sections/mouse with significance per individual mouse and overall. Error bars are ±SEM: (FIGS. 14A, 14A-1, 14B, and 14B-1) plaque areas (FIGS. 14C, 14C-1, 14D, 14D-1) perimeter values (FIGS. 14E and 14E-1) average feret diameters (FIGS. 14F and 14F-1) average integrated densities.

BRIEF DESCRIPTION OF THE SEQUENCES

Figure 1:
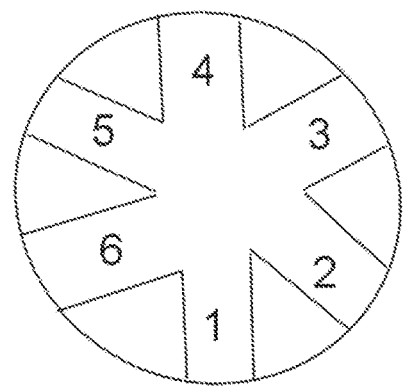
FIGS. 1 and 2 show pictures of a typical radial arm water maze device for cognitive disease behavioral testing in mice.
Figure 2:
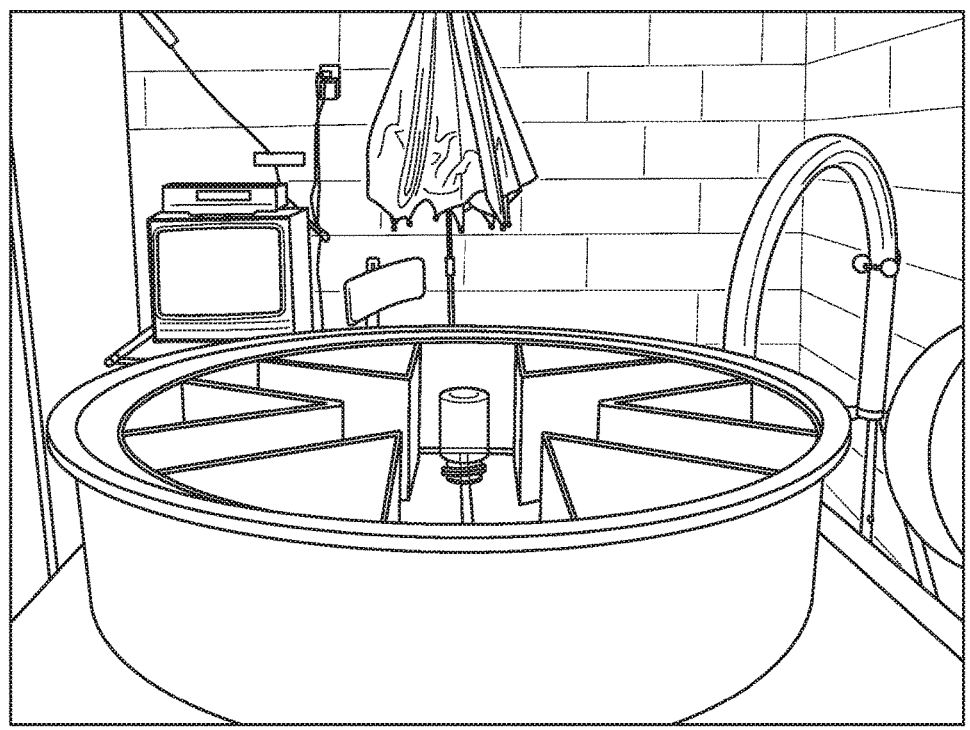

SEQ ID NO:1 is the amino acid sequence of a human GM-CSF polypeptide.

DETAILED DESCRIPTION OF THE INVENTION

The present invention provides methods for treating a person or animal having cognitive impairment wherein the method comprises administering to the person or animal an effective amount of one or more inflammatory mediators that are able to cross the blood brain barrier, or a polynucleotide(s) encoding the inflammatory mediator(s) (if the inflammatory mediator is a polypeptide), or a composition comprising the inflammatory mediator(s) or polynucleotide(s). The cognitive impairment can be a progressive cognitive impairment. In a specific embodiment, the cognitive impairment is caused by or results from Alzheimer's disease. In one embodiment, the cognitive impairment is caused by or results from stroke, Down's syndrome, dementia pugilistica, traumatic brain injury, AIDS-associated dementia, Lewy body disease, or Pick's disease. In one embodiment, the inflammatory mediator provides for an increase in cognitive responses in the brain and/or a neural protective effect. In one embodiment, the inflammatory mediator, or polynucleotide encoding the inflammatory mediator, is of human origin or sequence.

Inflammatory mediators contemplated within the scope of the present invention include, but are not limited to, fms-related tyrosine kinase 3 (Flt3) ligand, interleukin-6 (IL-6), macrophage migration inhibitory factor (MIF), interleukin-1 (IL-1), interleukin-3 (IL-3), erythropoietin (EPO), vascular endothelial growth factor A (VEGF-A), hypoxia-inducible transcription factor (HIF-1alpha), insulin like growth factor-1 (IGF-1), tumor necrosis factor (TNF), granulocyte colony-stimulating factor (G-CSF), granulocyte/macrophage colony-stimulating factor (GM-CSF), macrophage colony-stimulating factor (M-CSF), Stem Cell Factor (SCF), Darbepoetin (ARANESP), and metalloproteinases, or a functional fragment or variant thereof that exhibits substantially the same biological activity as the full-length or non-variant inflammatory mediator. Typically, to treat cognitive impairment in a human, the inflammatory mediator will have the sequence of the human protein or polynucleotide encoding it. The human sequences of the inflammatory mediators described herein are known in the art (see, for example, GenBank Accession Nos. NM_013520.3, NM_000799.2, NM_000759.2, M11220.1, NM_181054.2, NG_011713.1, NG_008851.1, NM_000588.3, NG_011640.1, NM_000757.4, NG_012099.1, NM_004530.4, NG_011468.1, NG_007462.1, and NG_008732.1). In one embodiment, the inflammatory mediator is GM-CSF, or a functional fragment or variant thereof that exhibits GM-CSF biological activity. In a specific embodiment, the GM-CSF is human GM-CSF. In one embodiment, GM-CSF and Darbepoetin and/or EPO are administered in a method of the invention for treating cognitive impairment. In another embodiment, G-CSF and Darbepoetin and/or EPO are administered. In addition, it is also contemplated that compounds capable of inducing production in a mammal of an inflammatory mediator of the invention, such as GM-CSF, which subsequently exerts an increase in cognitive responses in the brain, can be used according to the subject invention. Examples of such compounds include, but are not limited to, EPO and HIF-1α (Fisher (2003)). In one embodiment, the inflammatory mediator is administered or delivered to a non-neural tissue of the human or animal.

In one embodiment, an inflammatory mediator of the invention, or a polynucleotide encoding the inflammatory mediator, or a composition containing the inflammatory mediator or polynucleotide, is delivered at an effective dose subcutaneously or through infusion, intracranially, orally, parentally, intranasally, via inhalation, intrathecally, intramuscularly, sublingually, or by any other known and acceptable methods of drug delivery to a person or animal in need of such therapy.

The subject invention also concerns methods for decreasing or inhibiting the progression of cognitive impairment in a person or animal having memory problems associated with cognitive functions or related dementias. In one embodiment, a method of the invention comprises administering an effective amount of an inflammatory mediator of the invention, or a polynucleotide encoding the inflammatory mediator, or a composition containing the inflammatory mediator or polynucleotide, to the person or animal.

In vivo application of the inflammatory mediators of the invention, polynucleotides encoding the inflammatory mediators, and/or compositions containing them, can be accomplished by any suitable method and technique presently or prospectively known to those skilled in the art. The subject compounds can be formulated in a physiologically- or pharmaceutically-acceptable form and administered by any suitable route known in the art including, for example, oral, nasal, rectal, and parenteral routes of administration. As used herein, the term parenteral includes subcutaneous, intradermal, intravenous, intramuscular, intraperitoneal, and intrasternal administration, such as by injection. Administration of the subject inflammatory mediators of the invention can be a single administration, or at continuous or distinct intervals as can be readily determined by a person skilled in the art.

The inflammatory mediators of the subject invention, polynucleotides encoding the inflammatory mediators, and compositions comprising them, can also be administered utilizing liposome technology, slow release capsules, implantable pumps, and biodegradable containers. These delivery methods can, advantageously, provide a uniform dosage over an extended period of time. The inflammatory mediators of the invention can also be administered in their salt derivative forms or crystalline forms.

Inflammatory mediators of the subject invention and polynucleotides encoding the inflammatory mediators can be formulated according to known methods for preparing physiologically acceptable and/or pharmaceutically acceptable compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention may comprise between about 0.1% and 99%, and especially, 1 and 15% by weight of the total of one or more of the subject inflammatory mediator based on the weight of the total composition including carrier or diluent.

Inflammatory mediators of the invention, polynucleotides encoding the inflammatory mediators, and compositions comprising them, can be delivered to a cell either through direct contact with the cell or via a carrier means. Carrier means for delivering inflammatory mediators and compositions to cells are known in the art and include, for example, encapsulating the composition in a liposome moiety. Another means for delivery of inflammatory mediators and compositions of the invention to a cell comprises attaching the inflammatory mediators to a protein or nucleic acid that is targeted for delivery to the target cell. U.S. Pat. No. 6,960,648 and Published U.S. Patent Application Nos. 20030032594 and 20020120100 disclose amino acid sequences that can be coupled to another composition and that allows the composition to be translocated across biological membranes. Published U.S. Patent Application No. 20020035243 also describes compositions for transporting biological moieties across cell membranes for intracellular delivery. Inflammatory mediators can also be incorporated into polymers, examples of which include poly (D-L lactide-co-glycolide) polymer for intracranial delivery; poly[bis(p-carboxyphenoxy) propane:sebacic acid] in a 20:80 molar ratio (as used in GLIADEL); chondroitin; chitin; and chitosan.

While inflammatory mediators of the invention and polynucleotides encoding the inflammatory mediators can be administered by themselves, these inflammatory mediators can also be administered as part of a pharmaceutical composition. The subject invention thus further provides compositions comprising one or more inflammatory mediators in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

Other formulations of inflammatory mediators and polynucleotides encoding them suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Inflammatory mediators of the invention, polynucleotides encoding the inflammatory mediators, and compositions thereof, may be locally administered at one or more anatomical sites, optionally in combination with a pharmaceutically acceptable carrier such as an inert diluent. Inflammatory mediators of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the inflammatory mediators may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Inflammatory mediators, and polynucleotides encoding the inflammatory mediators, and compositions of the invention, including pharmaceutically acceptable salts or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions can be prepared by incorporating an inflammatory mediator of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, inflammatory mediators of the invention and polynucleotides encoding the inflammatory mediators may be applied in as a liquid or solid. However, it will generally be desirable to administer them topically to the skin as compositions, in combination with a dermatologically acceptable carrier, which may be a solid or a liquid. Inflammatory mediators can be applied in a formulation such as an ointment, cream, lotion, solution, tincture, or the like. Drug delivery systems for delivery of pharmacological substances to dermal sites can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver an inflammatory mediator to the skin are disclosed in U.S. Pat. Nos. 4,608,392; 4,992,478; 4,559,157; and 4,820,508.

Useful dosages of the inflammatory mediators, polynucleotides encoding the inflammatory mediators, and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The present invention also concerns pharmaceutical compositions comprising an inflammatory mediator of the invention, or a polynucleotide encoding the inflammatory mediator, in combination with a pharmaceutically acceptable carrier. Pharmaceutical compositions adapted for oral, topical or parenteral administration, comprising an amount of a compound constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The subject invention also concerns polynucleotide expression constructs that comprise a polynucleotide of the present invention comprising a nucleotide sequence encoding an inflammatory mediator of the present invention. In one embodiment, the polynucleotide encodes human GM-CSF, or a fragment or variant thereof that exhibits substantially the same activity as the full-length or non-variant GM-CSF.

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding an inflammatory mediator of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells. Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

For expression in prokaryotic systems, an expression construct of the invention can comprise promoters such as, for example, alkaline phosphatase promoter, tryptophan (trp) promoter, lambda $P_L$ promoter, β-lactamase promoter, lactose promoter, phoA promoter, T3 promoter, T7 promoter, or tac promoter (de Boer et al., 1983).

If the expression construct is to be provided in a plant cell, plant viral promoters, such as, for example, the cauliflower mosaic virus (CaMV) 35S (including the enhanced CaMV 35S promoter (see, for example U.S. Pat. No. 5,106,739)) or 19S promoter can be used. Plant promoters such as prolifera promoter, Ap3 promoter, heat shock promoters, T-DNA 1'- or 2'-promoter of *A. tumafaciens*, polygalacturonase promoter, chalcone synthase A (CHS-A) promoter from petunia, tobacco PR-1α promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Seed-specific promoters such as the promoter from a β-phaseolin gene (of kidney bean) or a glycinin gene (of soybean), and others, can also be used. Constitutive promoters (such as the CaMV, ubiquitin, actin, or NOS promoter), tissue-specific promoters (such as the E8 promoter from tomato), developmentally-regulated promoters, and inducible promoters (such as those promoters than can be induced by heat, light, hormones, or chemicals) are contemplated for use with the polynucleotides of the invention.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a polypeptide to an intended cellular and/or extracellular destination through the use of operably linked signal peptide sequence is contemplated for use with the inflammatory mediators of the invention. Chemical enhancers are cis-acting elements that increase gene transcription and can also be included in the expression construct. Chemical enhancer elements are known in the art, and include, but are not limited to, the CaMV 35S enhancer element, cytomegalovirus (CMV) early promoter enhancer element, and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides, vectors, and expression constructs of the subject invention can be introduced into a cell by methods known in the art. Such methods include transfection, microinjection, electroporation, lipofection, cell fusion, calcium phosphate precipitation, and by biolistic methods. In one embodiment, a polynucleotide or expression construct of the invention can be introduced in vivo via a viral vector such as adeno-associated virus (AAV), herpes simplex virus (HSV), papillomavirus, adenovirus, and Epstein-Barr virus (EBV). Attenuated or defective forms of viral vectors that can be used with the subject invention are known in the art. Typically, defective virus is not capable of infection after the virus is introduced into a cell. Polynucleotides, vectors, and expression constructs of the invention can also be introduced in vivo via lipofection (DNA transfection via liposomes prepared from synthetic cationic lipids) (Felgner et al., 1987). Synthetic cationic lipids (LIPOFECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced in vivo as naked DNA using methods known in the art, such as transfection, microinjection, electroporation, calcium phosphate precipitation, and by biolistic methods.

Polynucleotides and polypeptides of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules (encoding an inflammatory mediator of the invention) having sequences which are sufficiently homologous with the polynucleotide sequences encoding an inflammatory mediator of the invention so as to permit hybridization with that sequence under standard stringent conditions and standard methods (Maniatis, T. et al., 1982). As used herein, "stringent" conditions for hybridization refers to conditions wherein hybridization is typically carried out overnight at 20-25 C below the melting temperature (Tm) of the DNA hybrid in 6× SSPE, 5× Denhardt's solution, 0.1% SDS, 0.1 mg/ml denatured DNA. The melting temperature is described by the following formula (Beltz, G. A. et al., 1983):

$$Tm=81.5 \ C+16.6 \ Log \ [Na+]+0.41 \ (\% \ G+C)-0.61 \ (\% \ formamide)-600/length \ of \ duplex \ in \ base \ pairs.$$

Washes are typically carried out as follows:
(1) Twice at room temperature for 15 minutes in 1× SSPE, 0.1% SDS (low stringency wash).
(2) Once at Tm-20 C for 15 minutes in 0.2× SSPE, 0.1% SDS (moderate stringency wash).

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the sequences coding for an inflammatory mediator of the invention. The polynucleotide includes both the sense and antisense strands as either individual strands or in the duplex.

The subject invention also concerns kits comprising an inflammatory mediator, and/or polynucleotides encoding the inflammatory mediators, or a composition comprising an inflammatory mediator, or a compound or agent that induces production of the inflammatory mediator of the invention in one or more containers. Kits of the invention can optionally include pharmaceutically acceptable carriers and/or diluents. A kit of the invention can comprise one or more of fms-related tyrosine kinase 3 (Flt3) ligand, interleukin-6 (IL-6), macrophage migration inhibitory factor (MIF), interleukin-1 (IL-1), interleukin-3 (IL-3), erythropoietin (EPO), vascular endothelial growth factor A (VEGF-A), hypoxia-inducible transcription factor (HIF-1alpha), insulin like growth factor-1 (IGF-1), tumor necrosis factor (TNF), granulocyte colony-stimulating factor (G-CSF), granulocyte/macrophage colony-stimulating factor (GM-CSF), macrophage colony-stimulating factor (M-CSF), and metalloproteinases. In one embodiment, a kit of the invention includes one or more other components, adjuncts, or adjuvants as described herein. In one embodiment, a kit of the invention includes instructions or packaging materials that describe how to administer an inflammatory mediator or composition of the kit. Containers of the kit can be of any suitable material, e.g., glass, plastic, metal, etc., and of any suitable size, shape, or configuration. In one embodiment, an inflammatory mediator of the invention is provided in the kit as a solid, such as a tablet, pill, or powder form. In another embodiment, an inflammatory mediator of the invention is provided in the kit as a liquid or solution. In one embodiment, the kit comprises an ampoule or syringe containing a compound and/or agent of the invention in liquid or solution form.

The subject invention also concerns methods for identifying a compound that stimulates the activities of GM-CSF and its biological activities in reducing cognitive impairment.

The subject invention also concerns methods for identifying a compound that competitively inhibits the activities of GM-CSF and its biological activities in reducing cognitive impairment.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such human and non-human species.

The following terms are intended to have the meanings presented therewith below and are useful in understanding the description of the present invention and are not meant to limit the scope of the invention.

The term "neural cell" means any cell of neurological origin (e.g., brain, spinal cord) including sensory, transmittal and motor cells from the central nervous system or the peripheral nervous system such as a neuron, a glial, astrocyte, etc.

The term "amyloid beta peptide" means amyloid beta peptides processed from the amyloid beta precursor protein (APP). The most common peptides include amyloid beta peptides 1-40, 1-42, 11-40 and 11-42. Other species of less prevalent amyloid beta peptides are described as y-42, whereby y ranges from 2-17, and 1-x whereby x ranges from 24-39 and 41.

The term "carrier" means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or nonionic surfactants such as TWEEN, polyethylene glycol (PEG), and PLURONICS.

The term "contact" or "contacting" means bringing at least two moieties together, whether in an in vitro system or an in vivo system.

The term "condition" or "disease" means the overt presentation of symptoms (i.e., illness) or the manifestation of abnormal clinical indicators (e.g., biochemical indicators), or a genetic or environmental risk of or propensity for developing such symptoms or abnormal clinical indicators.

The term "endogenous" shall mean a material that an animal naturally produces. Endogenous in reference to, for example and not limitation, the term "kinase" shall mean that which is naturally produced by an animal, such as a mammal (for example, and not limitation, a human) or a virus. In contrast, the term non-endogenous in this context shall mean that which is not naturally produced by an animal, such as a mammal (for example, and not limitation, a human) or a virus. Both terms can be utilized to describe both "in vivo" and "in vitro" systems. For example, and not limitation, in a screening approach, the endogenous or non-endogenous kinase may be in reference to an in vitro screening system. As a further example, and not limitation, where the genome of a mammal has been manipulated to include a non-endogenous constitutively activated kinase, screening of a candidate compound by means of an in vivo system is viable.

The term "inhibit" or "inhibiting" or "suppress" or "suppressing" or "suppressive," in relationship to the term "response" means that a response is decreased or prevented in the presence of a compound as opposed to in the absence of the compound.

The term "ligand" means an endogenous, naturally occurring molecule specific for an endogenous, naturally occurring receptor.

The term "pharmaceutically acceptable prodrugs" as used herein means the prodrugs of the compounds useful in the present invention, which are, within the scope of sound medical judgment, suitable for use in contact with the tissues of patients with undue toxicity, irritation, allergic response commensurate with a reasonable benefit/risk ratio, and effective for their intended use of the compounds of the invention. The term "prodrug" means a compound that is transformed in vivo to yield an effective compound useful in the present invention or a pharmaceutically acceptable salt, hydrate or solvate thereof. The transformation may occur by various mechanisms, such as through hydrolysis in blood. The compounds bearing metabolically cleavable groups have the advantage that they may exhibit improved bioavailability as a result of enhanced solubility and/or rate of absorption conferred upon the parent compound by virtue of the presence of the metabolically cleavable group, thus, such compounds act as pro-drugs. A thorough discussion is provided in Bundgaard (1985), Widder et al. (1985), Krogsgaard-Larsen and Bandaged (1991), Bundgard (1992), Nielsenw and Bundgaard (1988), Nakeya et al. (1984), Higuchi and Stella (1987), which are incorporated herein by reference. An example of the prodrugs is an ester prodrug. "Ester prodrug" means a compound that is convertible in vivo by metabolic means (e.g., by hydrolysis) to an inhibitor compound according to the present invention. For example an ester prodrug of a compound containing a carboxy group may be convertible by hydrolysis in vivo to the corresponding carboxy group.

The term "pharmaceutically acceptable salts" refers to the non-toxic, inorganic and organic acid addition salts, and base addition salts, of compounds of the present invention. These salts can be prepared in situ during the final isolation and purification of compounds useful in the present invention.

The term "pharmaceutical excipients" refers to non-toxic adjuvants or compounds which can be added to the present invention which is capable of enhancing the biologically active effects of the peptide or its absorbancy in the body.

The term "polypeptide" relates to a protein made up of any one of the natural or synthetic amino acids and their equivalents. In the present invention, a polypeptide can mean, for example, the amino acid sequence of a GM-CSF protein or a biologically active equivalent thereof. In certain instances, any one of the naturally occurring amino acids can be replaced with a functional amino acid without changing the biological activity of the peptide. For example, peptides are short, sequence- and length-specific oligomers composed of amino acids. These familiar biomolecules are ubiquitous in living cells and assume myriad roles, including cell receptor ligand, endogenous antibiotic, and even components of pulmonary surfactant. Each role assumed by a bioactive peptide will typically correspond to a unique three-dimensional structure. In this way, nature has exquisitely refined bioactive peptide sequences and activities through evolution and, naturally, there has been significant interest in exploiting these molecules as pharmaceutical lead compounds. Often second generation pharmaceutical therapies have focused on the creation of non-natural peptide mimics. These 'peptidomimetics' can be based on any oligomer that mimics peptide primary structure through use of amide bond isosteres and/or modification of the native peptide backbone, including chain extension or heteroatom incorporation. Peptidomimetic oligomers are often protease-resistant, and may have reduced immunogenicity and improved bioavailability relative to peptide analogues. In addition to primary structural mimicry, a select subset of the sequence-specific peptidomimetic oligomers, the so-called 'foldamers,' exhibits well-defined secondary structural elements such as helices, turns and small, sheet-like structures. When a peptide's bioactivity or its biological equivalent is contingent upon a precise 3-D structure, the capacity of a biomimetic oligomer to fold can be indispensable. Examples of simple peptidomimetics include azapeptides, oligocarbamates and oligoureas, and common foldamer examples include β-peptides, γ-peptides, oligo(phenylene ethyylenes), vinylogous sulfonopeptides and poly-N-substituted glycines (peptoids). Therefore, peptidomimetics of a an inflammatory mediator of the present invention, such as GM-CSF polypeptide are within the scope of the present invention.

The term "solvate" means a physical association of a compound useful in this invention with one or more solvent molecules. This physical association can include hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term "effective amount" or "therapeutically effective amount" means that amount of a compound or agent that will elicit the biological or medical response of a subject that is being sought by a medical doctor or other clinician. In particular, with regard to treating a neuronal disorder, the term "effective amount" is intended to mean that effective doses of medicament which can decrease cognitive impairment in a subject. The typical weight for an average mouse is approximately 0.025 kg with a metabolic rate of approximately 7.2 times that of a human. The typical weight for an average person is approximately 70 kg. With the standard weight and metabolic rate adjustments, it is within the scope of one of ordinary skill in the art to be able to derive effective doses for therapies of medicament of the invention as described herein. For example, effective amounts within the scope of the invention are equivalent mouse doses which is within about 5 mcg/day for a period as needed to achieve cognitive effects which is within about 2 mg/day for humans. Alternatively, effective doses for humans can also be within the range of about 50 mcg/day to about 2 mg/day, or alternatively 50 mcg/day, or 100 mcg/day, or 250 mcg/day, or 500 mcg/day, or 750 mcg/day or 1 mg/day or 1.25 mg/day, or 1.5 mg/day or 2 mg/day, or 2.25 mg/day, or 2.5 mg/day or adjusted as needed for the weight, metabolism and metabolic needs of the individual to at least achieve the effective cognitive effects of such individual.

The term "treating" means an intervention performed with the intention of reversing or preventing the development or altering the pathology of, and thereby alleviating a disorder, disease or condition, including one or more symptoms of such disorder, disease, or condition. Preventing refers to prophylactic or preventative measures. The related term "treatment," as used herein, refers to the act of treating a disorder, symptom, disease or condition, as the term "treating" is defined above.

Flt3 ligand is a ligand for the FLT3 tyrosine kinase receptor and belongs to a small group of growth factors that regulate proliferation of early hematopoietic cells. Multiple isoforms of Flt3 ligand have been identified. The predominant form is the transmembrane form, which is biologically active on the cell surface. When proteolytically cleaved the transmembrane isoform generates a soluble form, which is also biologically active. Flt3 ligand binds to cells expressing the tyrosine kinase receptor Flt3. Flt3 ligand alone cannot stimulate proliferation, but synergizes well with other Colony Stimulating Factors (CSFs) and interleukins to induce growth and differentiation.

Interleukin 6 (IL-6) is a multifunctional 24 kDa protein originally discovered in the medium of RNA stimulated fibroblastoid cells. It is upregulated by IL-1, TNF, PDGF, IFN-beta, TNF-alpha, NGF, IL-17 and downregulated by glucocorticoids IL-4, TGF-beta. IL-6 appears to be directly involved in the responses that occur after infection and cellular injury, and it may prove to be as important as IL-1 and TNF-alpha in regulating the acute phase response. IL-6 has also been implicated in regulating adipose mass. IL-6 is reported to be produced by fibroblasts, activated T cells, activated monocytes or macrophages and endothelial cells. It acts upon a variety of cells including fibroblasts, myeloid progenitor cells, T cells, B cells and hepatocytes. In addition, IL-6 appears to interact with IL-2 in the proliferation of T lymphocytes. IL-6 potentiates the proliferative effect of IL-3 on multipotential hematopoietic progenitors.

Macrophage migration inhibitory factor (MIF), originally described as a T lymphocyte-derived factor that inhibited the random migration of macrophages, is an enigmatic cytokine for almost 3 decades. In recent years, the discovery of MIF as a product of the anterior pituitary gland and the cloning and expression of bioactive, recombinant MIF protein have led to the definition of its critical biological role in vivo. MIF has the unique property of being released from macrophages and T lymphocytes that have been stimulated by glucocorticoids. Once released, MIF overcomes the inhibitory effects of glucocorticoids on TNF alpha, IL-1 beta, IL-6, and IL-8 production by LPS-stimulated monocytes in vitro and suppresses the protective effects of steroids against lethal endotoxemia in vivo. MIF also antagonizes glucocorticoid inhibition of T-cell proliferation in vitro by restoring IL-2 and IFN-gamma production. This observation has resulted in the identification of a pivotal role for MIF within the immune system and fills an important gap in our understanding of the control of inflammatory and immune responses. Glucocorticoids have long been considered to be an integral component of the stress response to infection or tissue invasion and serve to modulate inflammatory and immune responses. MIF is the first mediator to be identified that can counter-regulate the inhibitory effects of glucocorticoids and thus plays a critical role in the host control of inflammation and immunity.

Tumor necrosis factor (TNF) is a member of a superfamily of proteins, each with 157 amino acids, which induce necrosis (death) of tumor cells and possess a wide range of proinflammatory actions. Tumor necrosis factor is a multi-functional cytokine with effects on lipid metabolism, coagulation, insulin resistance, and the function of endothelial cells lining blood vessels.

Interleukin-1 (IL-1) is one of the first cytokines ever described. Its initial discovery was as a factor that could induce fever, control lymphocytes, increase the number of bone marrow cells and cause degeneration of bone joints. At this time, IL-1 was known under several other names including endogenous pyrogen, lymphocyte activating factor, haemopoetin-1 and mononuclear cell factor, amongst others. It was around 1984-1985 when scientists confirmed that IL-1 was actually composed of two distinct proteins, now called IL-1α and IL-1β.

Interleukin-3 (IL-3), a 152 amino acid protein, usually glycosylated, was originally found as a T lymphocyte-derived factor which induced 20alpha-hydroxysteroid dehydrogenase synthesis within hematopoietic cells. It is secreted by activated T cells and binds to the IL-3 receptor that heterodimerizes with a common beta c receptor subunit, which is shared by GM-CSF and IL-5. IL-3 functions similarly to GM-CSF and the human IL-3 gene is located on chromosome 5, nine kilobases away from the GM-CSF gene. IL-3 has been shown to support the proliferation of many hematopoietic cell types and is involved in a variety of cell activities such as cell growth, differentiation and apoptosis.

Erythropoietin (EPO) is a 30.4 kDA glycoprotein hormone, produced mainly by peritubular fibroblasts of the renal cortex, and it works to protect erythrocytes from apoptosis, as well as promote proliferation and maturation of erythroid progenitor cells through synergistic actions with other growth factors (IGF-1, IL-3, and GM-CSF). Blood oxygenation is thought to regulate EPO's expression through constitutively-synthesized transcription factors called hypoxia-inducible factors. EPO has also been reported to have neuroprotective and angiogenic properties.

Vascular endothelial growth factor A (VEGF-A) is a multi-functional protein that belongs to the platelet-derived growth factor family and is involved in vasculogenesis and angiogenesis. It is produced in hypoxic cells and released by HIF-1α expression to bind to cell surface receptors VEGFR-1 (Flt-1) or VEGFR-2 (KDR/Flk-1), inducing various functions accordingly. It has been shown to stimulate endothelial cell mitogenesis and migration, vasodilation, and be chemotactic to monocytic-lineage hematopoietic cells.

Hypoxia-inducible transcription factor alpha (HIF-1α) is a transcription factor that responds to changes in available cellular oxygen. In normoxic conditions, it is rapidly degraded by the proteasome upon prolyl hydroxylation by HIF prolyl-hydroxylase, which subsequently induces its ubiquitination. Hypoxic conditions prevents this prolyl hydroxylation, and HIF-1α is stabilized and acts to upregulate several genes which promote hypoxic survival, such as EPO, and VEGF. HIF-1α thus increases vasculogenesis and angiogenesis through upregulation of these genes.

Insulin-like growth factor 1 (IGF-1) is a 70 amino acid polypeptide protein hormone similar in molecular structure to insulin and is produced primarily by the liver. IGF-1 binds to the IGF-1 receptor (IGF-R) and the insulin receptor (IR), and is a potent activator of the cell growth and anti-apoptotic AKT signaling pathway. Although produced throughout life, its expression is lowest in infancy and old age, and IGF-R and IR have been reported to be reduced in Alzheimer's disease (AD) and correlate with neurodegeneration. IGF-1 has also been implicated in the pathogenesis of type 2 diabetes, a positive-risk factor for AD, through vascular complications resulting from its deficient signaling with insulin and EPO.

Granulocyte colony-stimulating factor (G-CSF or GCSF) is a colony-stimulating factor hormone. It is a glycoprotein, growth factor or cytokine produced by a number of different tissues to stimulate the bone marrow to produce granulocytes and stem cells. G-CSF then stimulates the bone marrow to release them into the blood. It also stimulates the survival, proliferation, differentiation, and function of neutrophil precursors and mature neutrophils. G-CSF is also known as colony-stimulating factor 3 (CSF-3).

Granulocyte-macrophage colony-stimulating factor (GM-CSF) is a protein secreted by macrophages, T cells, mast cells, endothelial cells and fibroblasts. GM-CSF is a cytokine that functions as a white blood cell growth factor. GM-CSF stimulates stem cells to produce granulocytes (neutrophils, eosinophils, and basophils), monocytes, and dendritic cells. Monocytes exit the circulation and migrate into tissue, whereupon they mature into macrophages. It is thus part of the immune/inflammatory cascade, by which activation of a small number of macrophages can rapidly lead to an increase in their numbers, a process crucial for fighting infection. The active form of the protein is found extracellularly as a homodimer.

Macrophage colony-stimulating factor (M-CSF or CSF-1) is a secreted cytokine which influences hemopoietic monocytic cells to proliferate and differentiate into macrophages or other related cell types, such as osteoclasts, as well as activating mature macrophages, osteoclasts, and microglia. M-CSF has been recently reported to have decreased expression in AD patients, and its peripheral administration in an amyloidosis murine animal model of AD ameliorated amyloid deposition and cognitive function.

Metalloproteinases (or metalloproteases) constitute a family of enzymes from the group of proteinases, classified by the nature of the most prominent functional group in their active site. There are two subgroups of metalloproteinases: exopeptidases called metalloexopeptidases and endopeptidases called metalloendopeptidases. Well known metalloendopeptidases include ADAM proteins and matrix metalloproteinases.

Darbepoetin is a novel erythropoetin-stimulating factor (NESP) that has a longer plasma half-life than EPO, and only varies by native human EPO at 5 amino acid positions. Darbepoetin would also be expected to act synergistically with GM-CSF in the maturation and proliferation of the burst-forming and colony-forming erythroid units to the normoblast stage of erythropoiesis (Fisher (2003)). Erythropoiesis is important in Alzheimer's disease due to oxygenation of neuronal cells, and to clearance of complement-bound circulating amyloid beta proteins via the expression of complement receptor 1 (CR1) on the erythrocyte surface (Rogers et al. (2006); Cadman and Puttfarcken (1997); Helmy et al. (2006)).

Stem Cell Factor (SCF) is a cytokine which has been reported to stimulates the growth and development of primitive multipotential and unipotential hematopoietic stem cells either alone or in combination with other cytokines such as GM-CSF, G-CSF, and EPO (Fisher (2003)). SCF also acts to stimulate the function of mature granulocytes (Czygier et al. (2007)).

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Radial Arm Water Maze Testing—Working (short-term) memory is evaluated in the radial arm water maze (RAWM) task, using the same pool that was involved in both Morris water maze and platform recognition testing. This task also uses the same clear platform and visual cues as in Morris maze testing.

For the radial arm water maze task of spatial working memory, an aluminum insert was placed into a 100 cm circular pool to create 6 radially distributed swim arms emanating from a central circular swim area. An assortment of 2-D and 3-D visual cues surrounded the pool. The number of errors prior to locating which one of the 6 swim arms contained a submerged escape platform (9 cm diameter) was determined for 5 trials/day over 8 days of pre-treatment testing and 4 days of post-treatment testing. There was a 30-min time delay between the 4th trial (T4; final acquisition trial) and 5th trial (T5; memory retention trial). The platform location was changed daily to a different arm, with different start arms for each of the 5 trials semi-randomly selected from the remaining 5 swim arms. During each trial (60 s maximum), the mouse was returned to that trial's start arm upon swimming into an incorrect arm and the number of seconds required to locate the submerged platform was recorded. If the mouse did not find the platform within a 60-s trial, it was guided to the platform for the 30-s stay. The numbers of errors and escape latency during trials 4 and 5 are both considered indices of working memory and are temporally similar to the standard registration/recall testing of specific items used clinically in evaluating AD patients.

Following post-treatment completion of RAWM testing (4 days), all mice were further evaluated in a novel cognitive interference task for 6 days. This task involves two radial arm water maze set-ups in two different rooms, and 3 different sets of visual cues. The task required animals to remember a set of visual cues, so that following interference with a different set of cues, the initial set of cues can be recalled to successfully solve the radial arm water maze task. A set of five behavioral measures were examined. Behavioral measures were: A1-A3 (Composite three-trial recall score from first 3 trials performed in RAWM "A"), "B" (proactive interference measure attained from a single trial in RAWM "B"), A4 (retroactive interference measure attained during a single trials in RAWM "A"), and "A5" (delayed-recall measure attained from a single trial in RAWM "A" following a 20 minute delay between A4 and A5). As with the stand RAWM task, this interference task involved the platform location being changed daily to a different arm for both of the RAWM set-ups utilized, and different start arms for each day of testing for both RAWM set-ups. For A1 and B trials, the animal was initially allowed one minute to find the platform on its own before it was guided to the platform. Then the actual trial was performed in each case.

Mouse recombinant GM-CSF was used in each experiment using PS/APP mice. 5 µg per injection were reconstituted in saline and injected into treated mice subcutaneously over the period of the study as outlined below.

Cohort 1: 29 mice, F8 White Generation, DOB Apr. 20-May 7, 2007

8 APP mice, 21 Non-transgenic mice

Pre-testing RAWM: Mice 1 year old

8 Days of RAWM: Apr. 25-May 2, 2008

15-Day delay between pre-testing and starting injections

Begin Treatment May 17, 2008

10 Days of injections (5 µg/day s.c.) before RAWM post-testing with daily injections throughout entire testing period.

Begin post-testing RAWM May 27, 2008-May 30, 2008; no testing May 31, 2008-Jun. 1, 2008 but daily injections continued; begin Interference RAWM Jun. 2, 2008-Jun. 7, 2008

Additional mice added to study=Cohort 2

8 mice: F8 Bright Orange, DOB May 27, 2007, 3 APP/PS1, 4 APP

F7 Light Blue, DOB Jun. 27, 2007, 1 APP

Pre-testing RAWM

8 Days of RAWM: May 12-May 19, 2008

Started 17 days after cohort 1

15-Day delay between pre-testing and starting injections

Begin Treatment Jun. 3, 2008

10 Days of injections (5 µg/day s.c.) before RAWM post-testing with injections each day throughout entire testing period.

Begin post-testing RAWM Jun. 12, 2008-Jun. 15,2008; no testing Jun. 16, 2008-Jun. 17, 2008 but daily injections continued; Begin Interference RAWM Jun. 18, 2008-Jun. 23, 2008

Figures 3, 4:
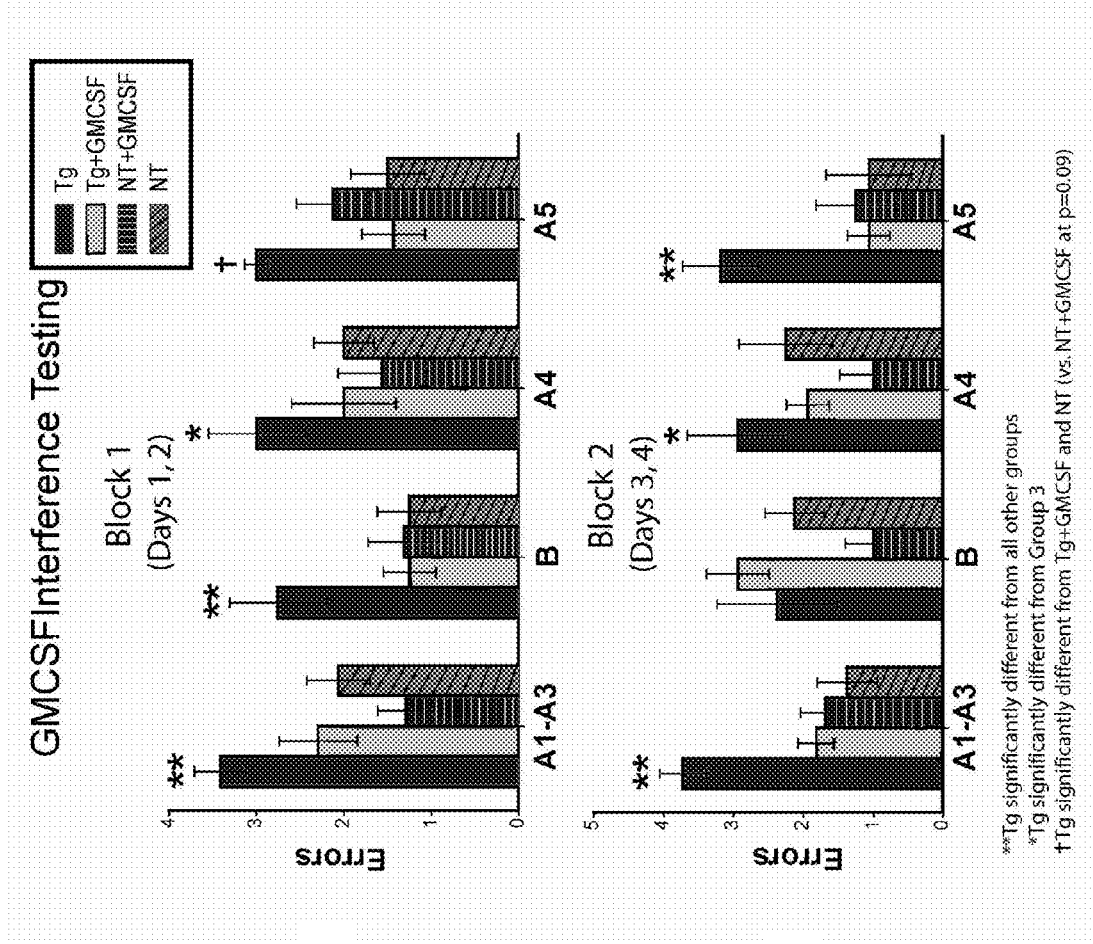
FIGS. 3 and 4 show GMCSF Interference testing—Block 1 (FIG. 3) and Block 2 (FIG. 4).

Results:

FIGS. 3, 4, and 7 depict the results of the GM-CSF testing. FIGS. 7A-7D: Standard RAWM errors (4 days of testing; two 2-day blocks). For both Blocks 1 and 2 of testing, the untreated APP transgenic group shows clear impairment compared to all or most other groups on working memory trials T4 and T5. Performance over all post-treatment days of testing revealed that the untreated APP transgenic group was substantially impaired compared to all 3 other groups, which performed similarly to each other.

FIG. 7E: GM-CSF Interference Testing—Overall

The untreated APP transgenic group was very impaired in immediate recall trials (A1-A3) compared to all 3 other groups. The untreated APP transgenic group showed significantly impaired performance for both proactive (Trial B) and retroactive (Trial A4) interference trials compared to GM-CSF treated nontransgenic littermate controls. APP transgenic GM-CSF treated group performed no differently from treated and untreated nontransgenic littermate control groups on these trials. The untreated APP transgenic group was very impaired in the delayed recall trial (A5) compared to all 3 other groups, which did not differ from one another in performance.

FIGS. 3 and 4: GM-CSF Interference Testing—Block 1 and Block 2.

During both blocks, the untreated APP transgenic group showed impaired immediate recall (A1-A3) and impaired delayed recall (A5) compared to all 3 other groups, which exhibited no differences from one another in performance. During Block 1, the APP untreated transgenic group showed a selective impairment in proactive interference performance (Trial B). All the other groups performed much better during this trial and performances was identical to one another. During both blocks, the untreated APP transgenic group was impaired in retroactive interference (A4) compared to the GM-CSF treated nontransgenic littermate group.

It is evident from both standard RAWM testing and RAWM interference testing that the untreated APP transgenic group is consistently impaired in working memory, proactive interference, retroactive interference, and delayed recall compared to the other 3 groups. By contrast, the GM-CSF treated APP transgenic group's performance is never statistically different from that of the nontransgenic littermates which were GM-CSF treated or untreated. It is clearly indicated that the untreated APP transgenic group performed much poorer across multiple cognitive measures in comparison to the other 3 groups.

Figure 5A:
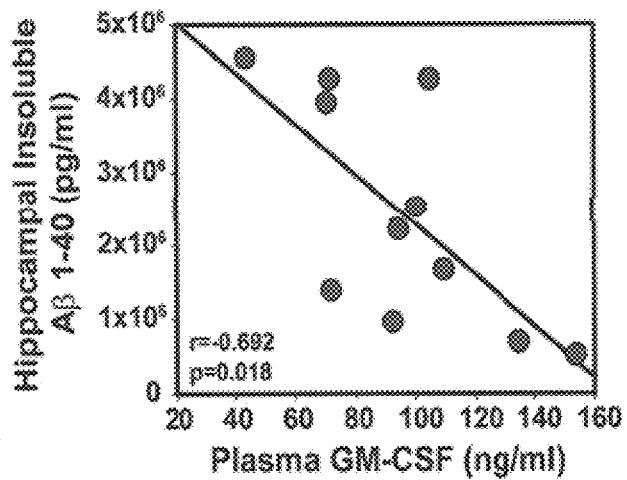
FIGS. 5A and 5B show decreasing levels of insoluble amyloid beta levels in the hippocampus of mice.
Figure 5B:
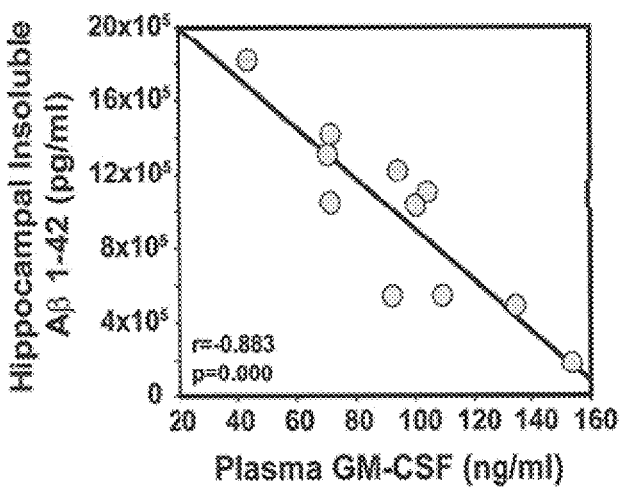
Figure 5C:
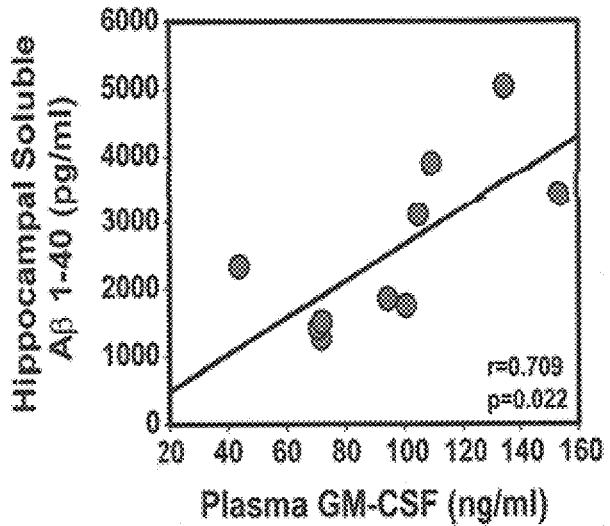
FIG. 5C shows an increase in levels of soluble amyloid beta levels in hippocampus of mice with increasing plasma concentrations of GM-CSF.
Figure 6A:
FIGS. 6A and 6B.
Figure 6B:
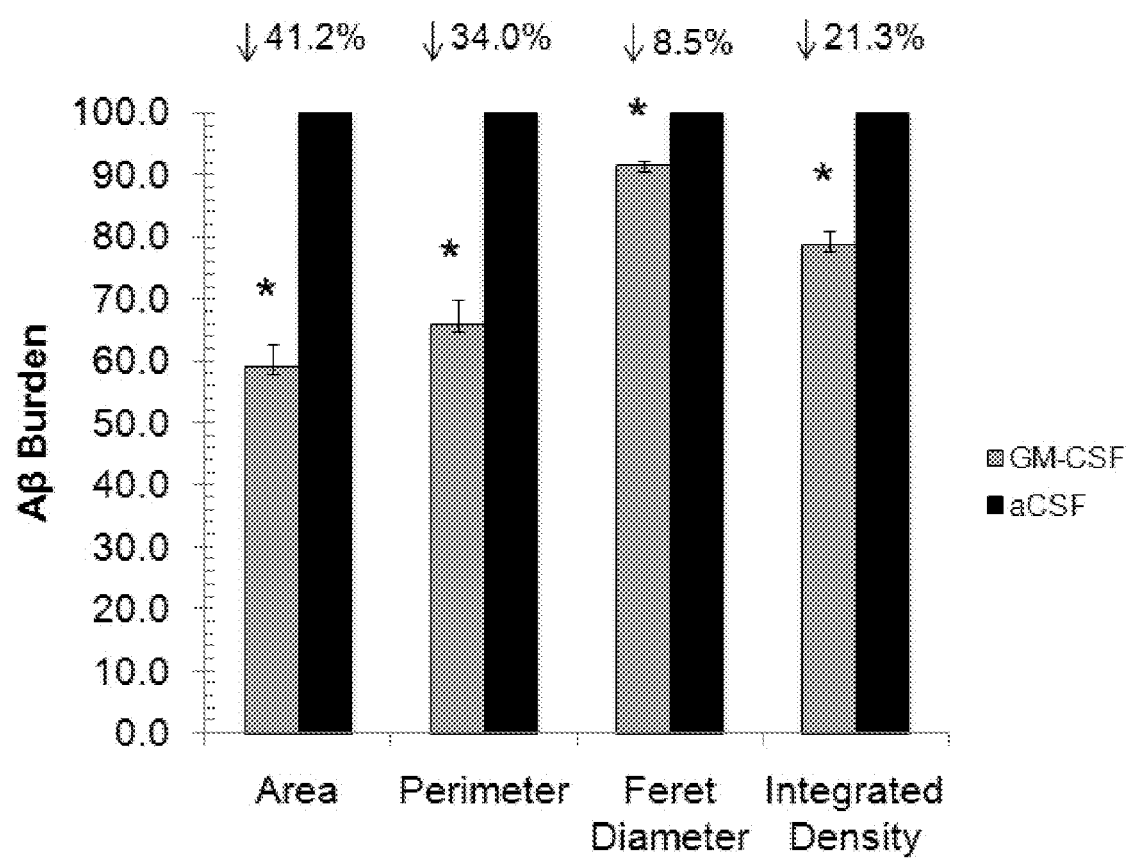
Figure 9E:
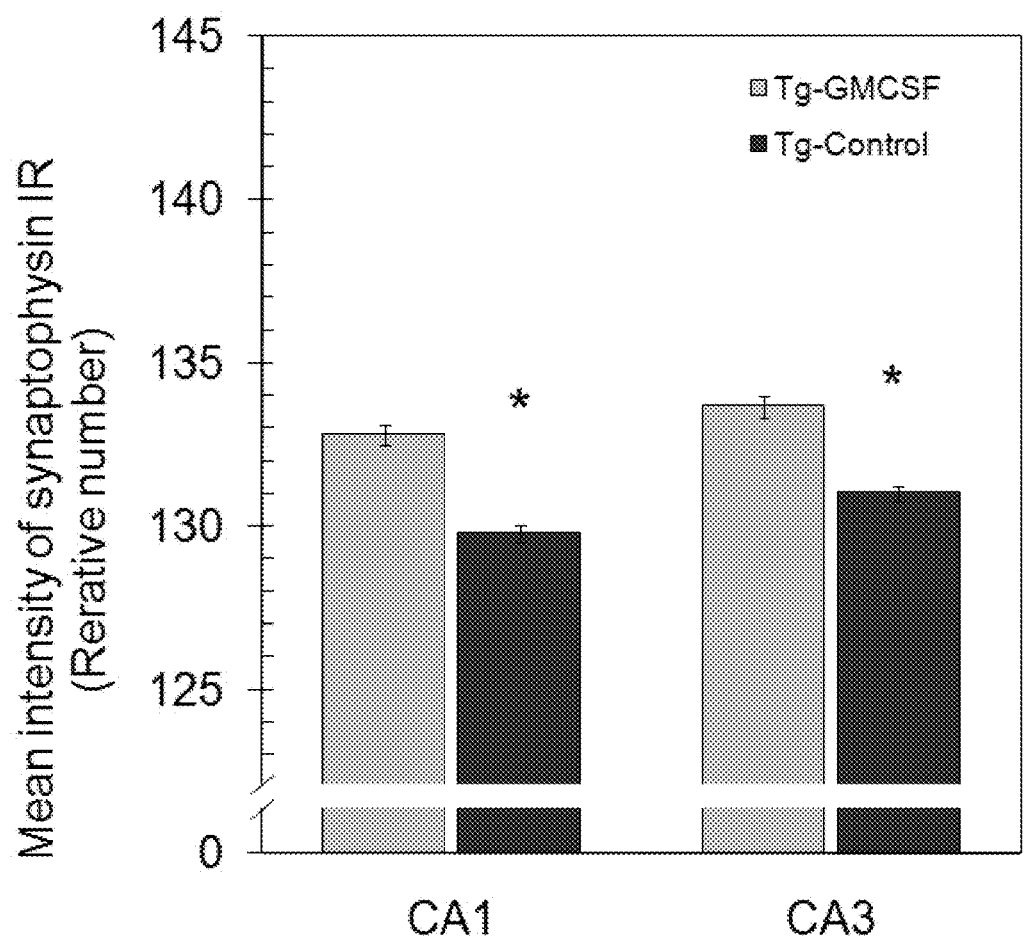

Further, in a separate set of experiments wherein groups of mice were treated with caffeine and plasma levels of GM-CSF were ascertained to determine if there was a correlation between GM-CSF levels and amyloid beta levels in the hippocampus, it was found that there were strong inverse correlations between plasma GM-CSF and hippocampal insoluble A-beta levels, e.g. see FIGS. 5A and 5B. By contrast, there was a significant positive correlation between plasma GM-CSF and hippocampal soluble A-beta levels (see FIG. 5C). This separate observational study using animals in a different set of experiments suggested that GM-CSF was in some way removing insoluble deposited A-beta from the brain, resulting in increased soluble A-beta in the brain. Perhaps the elevated soluble A-beta is the transport mechanism for clearance of the beta plaques into the plasma. This may suggest a mechanism of cognitive benefits of GM-CSF. Other mechanisms which may explain the cognitive benefits of GM-CSF or its biological equivalents are possible and within the scope of the invention as described herein, would include neovascularization in the brain with increased cerebral blood flow, reductions in plaques and their associated inflammation, bone-marrow-derived neurogenesis, or neuroprotection against microvascular plaque-induced ischemia and resulting oxidative stress. It is also considerable that any combination of these mechanisms mentioned herein is considered as attributable to the effects of GM-CSF and its biological equivalents on cognitive benefits and would be within the scope of practice of the claimed invention as described herein.

Materials and Methods for Example 2

Transgenic Mice Involving Intracerebral Administration of CSFs. PS/APP mice were generated by crossing heterozygous PDGF-hAPP (V717F) mice with PDGF-hPS1 (M146L) on both Swiss Webster and C57BL/6 backgrounds. Transgene detection was performed using comparative real-time PCR (Bio-Rad iCycler-Hercules, Calif.). The pathogenic phenotype in this model is robust amyloid plaque accumulation beginning 6-8 months of age. All procedures involving experimentation on animals were performed in accordance with the guidelines set forth by the University of South Florida Animal Care and Use Committee.

Figure 10:
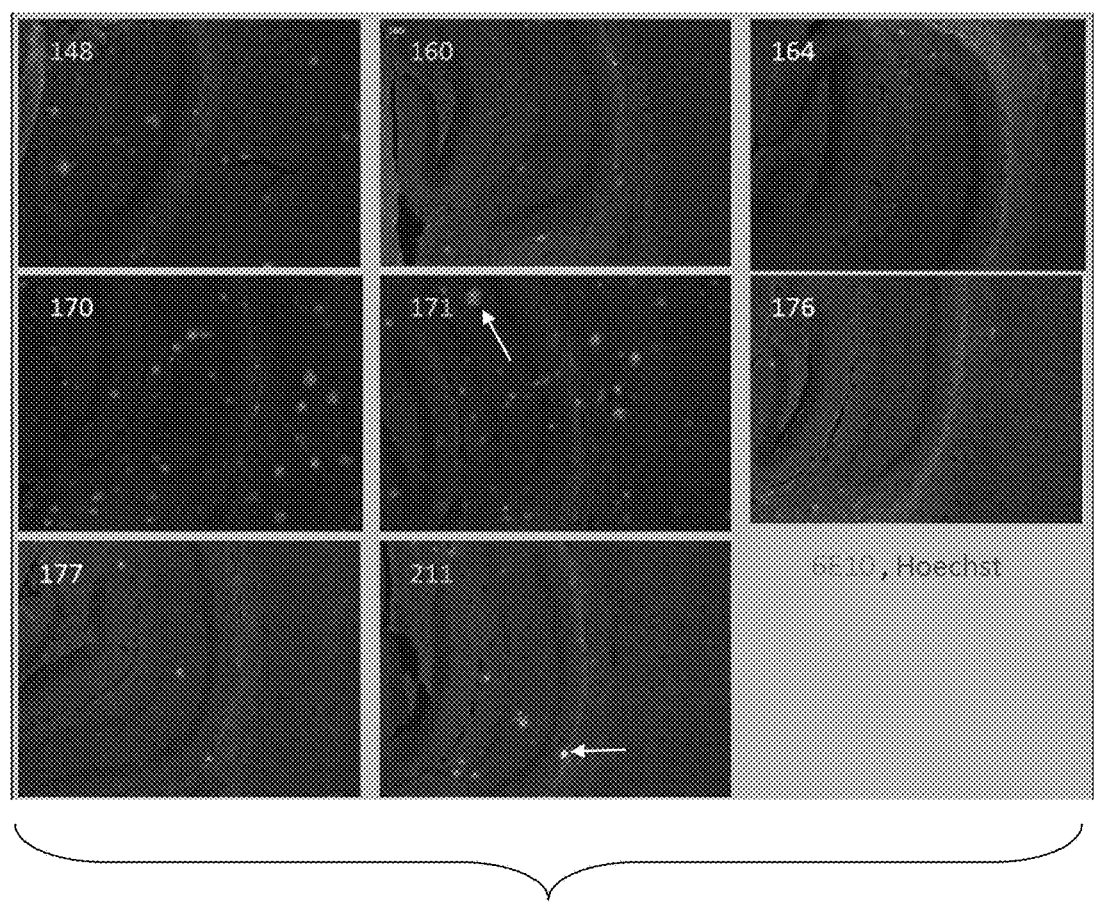
FIG. 10 shows significant variation of amyloid plaque load between mice. PS/APP mice of similar age (numbered sequentially according to date of birth) after bilateral intracerebroventricular infusions of M-CSF. Mouse numbers 148, 160, 171, and 211 received M-CSF and mice 164, 170, 176, and 177 received aCSF. Infusions lasted 2 weeks. Cryosectioned at 14 µm and stained with 6E10/Alexa 488 and Hoechst. Bright green spots indicate amyloid plaques. Pictures taken at 5×.

Intracranial Infusions of M-CSF. Animals (PS/APP, all 8.8-9.6 months, 25-35 g, both genders) were anesthetized with 1-2% isoflurane, shaved and scrubbed with 10% Betadine solution at the site of incision, and placed into a stereotaxic frame (Kopf Instruments, Tujunga, Calif.). A small (4 cm) incision was made, exposing the skull, and double bladed scissors were used to form a subcutaneous pocket along the animal's back into which osmotic minipumps (Alzet model 1004, Durect Corp., Cupertino, Calif.) were inserted. Two holes were drilled into the skull (from Bregma −0.1 mm anterior-posterior, +/−0.9 mm medial-lateral, and the 30 gauge catheters were inserted at depth of 3.0 mm, corresponding to the lateral ventricles). Leading from the Alzet pump is a proprietary catheter system (International Application No. PCT/US08/73974) with the delivery tips fashioned to the contours of the skull rather than the commercially-available pedestal cannula. This completely subcutaneously-contained system allows bilateral intracerebral infusion of test substances. This capability overcomes the problem of the variance in amyloid deposition between animals (see FIG. 10), by allowing for infusion into each hemisphere, where a test substance can be delivered ipsilaterally and vehicle contralaterally, effectively making each animal its own control. Moreover, the scalp heals and reduces chronic inflammation and irritation to the mice from the open wound, seen with pedestal-mounted cannula usage. Once the cannulae are both inserted, they are affixed to the skull using Locktite 454 adhesive (Plastics One, Roanoke, Va.) and secured with 1 cm diameter nitrile. After the adhesive cures, the scalp is sutured with 6-7 silk sutures and the animal is given an immediate dose of ketoprofen (10 mg/kg) and again every 6 hours as needed for another 48 hours.

M-CSF was bilaterally infused directly into the lateral ventricles (5 µg/day) for 14 days using Alzet model 1004 with an average flow rate of 0.12 µL/hour. The pumps and catheters were primed for 48 hours in a 37° C. water bath prior to implantation. After the 14-day period, the animals are given an overdose (~100 mg/kg, i.p.) of sodium pentobarbital followed by transcardial perfusion with 0.9% cold saline.

Stereotaxic Injection of CSFs. All 3 CSFs were stereotaxically-injected (5 µg/injection) into the (ipsilateral) hippocampus, with vehicle (artificial cerebrospinal fluid (aCSF)) injected contralaterally into four PS/APP mice each (all 10-12 months old, 25-35 g, both genders). Two holes were drilled into the skull (from bregma −2.5 mm anterior-posterior, +/−2.5 mm medial-lateral, and the 30 gauge needle inserted to a depth of 2.5 mm). Mice were euthanized and 0.9% cold saline-perfused 7 days later. Recombinant mouse GM-CSF (rmGM-CSF), recombinant murine G-CSF (rmG-CSF), and recombinant mouse M-CSF (rmM-CSF)

(R&D Systems) will be referred to as GM-CSF, G-CSF, and M-CSF throughout this publication.

Immunohistochemistry and Image Analysis of Intrahippocampal-injected Mice. Perfused brain tissues from the intrahippocampus-injected mice were fixed in 10% neutral buffered formalin for 24-36 hours and then placed through a sucrose gradient (10-30%) over another 72 hours. Brains were then frozen to the peltier (Physitemp, Clifton, N.J.) of the histoslide (Leica, Heerbruug, Switzerland) and sectioned coronally at 14 µm. Alternatively, selected brains were paraffin-embedded after 10% neutral buffered formalin fixation, sectioned at 5 µm, and adhered to slides. Deparaffination and antigen retrieval (boiled in 10 mM Sodium Citrate buffer for 20 min) were performed before immunohistochemical staining To significantly reduce cost of reagents and antibodies with paraffin-embedded slides, a novel magnetic immunohistochemical staining device was developed. Standard immunohistochemical techniques used anti-Aβ antibodies, i.e. 6E10 (1:1000), and MabTech's (1:5000) to immunolabel amyloid deposition followed by Alexa 488 and/or 564 secondary fluorophores (1:1000, 1:4000—Invitrogen), and Hoechst (Sigma) nuclear staining. The tissues were visualized on a Zeiss Imager.Z1 fluorescence microscope with a Zeiss Axiocam Mrm camera (Oberkochen, Germany) using Axiovision 4.7 software. Photomicrographs were taken at 10× and montaged with Axiovision Panarama Module to select equal areas from corresponding loci of each brain hemisphere. There were 5 coronal sections/mouse with 15-25 10× pictures/hemisphere analyzed (varied according to anterior-posterior location). Amyloid quantification was performed using ImageJ software program (developed at and available from National Institutes of Health). Briefly, each analyzed picture per coronal section was thresholded equally to the same standard deviation from the histogram mean, and we used the same area threshold to minimize background artifacts, and analyzed for area, perimeter, feret diameter, and integrated density parameters. The feret diameter is the longest distance across a given plaque, and the integrated density is the product of the area and the average gray value of the plaque's pixels.

Behavioral Transgenic Mouse Study Involving GM-CSF Treatment. Mice in this study were derived from the Florida Alzheimer's Disease Research Center transgenic mouse colony, wherein heterozygous mice carrying the mutant APPK670N, M671L gene (APPsw) are routinely crossed with heterozygous PS1 (Tg line 6.2) mice to obtain offspring consisting of APPsw/PS1, APPsw, PS1, and non-transgenic (NT) genotypes on a mixed C57/B6/SW/SJL background. Eleven APPsw, 4 APPsw/PS1, and 17 NT mice, all 12-months old, were selected for use in this study, and evaluated in the RAWM task of working memory for 8 days (see protocol below). Numerous experiments have revealed that various genotypes of AD perform equally once they reach cognitive impairment. Thus, the 15 Tg mice were divided into two groups, balanced in RAWM performance, with 2 APPsw mice included in each group. The 17 NT mice were also divided into two groups, balanced in RAWM performance. Two weeks following completion of pre-treatment testing, one group of Tg mice (n=7) and one group of NT mice (n=9) were started on a 10-day treatment protocol with GM-CSF (5 µg/day given subcutaneously), while animals in the control Tg and NT groups (n=8 per group) received daily vehicle (saline) treatment subcutaneously over the same 10-day period. On the 11th day of injections, all mice began evaluation for four days in the RAWM task, given 2 days of rest, then followed by an additional 4 days of testing in the novel Cognitive Interference task (see protocol below). Daily GM-CSF and saline injections were continued throughout the behavioral testing period. After completion of behavioral testing at 3 weeks into treatment, all mice were euthanatized, brains fixed as described above, and paraffin-embedded. Careful visual examination of all tissues upon necropsy revealed no morphological abnormalities, and the mice tolerated daily subcutaneous injections well.

Immunohistochemistry and Image Analysis of Subcutaneous GM-CSF-treated Mice.

Perfused brain tissues from the subcutaneously injected, behaviorally-tested mice were fixed in 10% neutral buffered formalin for 24-36 hours, and then paraffin-embedded. At the level of the hippocampus (bregma −2.92 mm to −3.64 mm), five 5-µm sections (150 µm apart) were made from each mouse brain using a sliding microtome, and mounted per slide. Immunohistochemical staining was performed following the manufacturer's protocol using a Vectastain ABC Elite kit (Vector Laboratories, Burlingame, Calif.) coupled with the diaminobenzidine reaction, except that the biothinylated secondary antibody step was omitted for Aβ immunohistochemical staining. The following primary antibodies were used for immunohistochemical staining: a biothinylated human Aβ monoclonal antibody (clone 4G8; 1:200, Covance Research Products, Emeryville, Calif.) and rabbit synaptophysin polyclonal antibody (undiluted, DAKO, Carpinteria, Calif.). For Aβ immunohistochemical staining, brain sections were treated with 70% formic acid prior to the pre-blocking step. Phosphate-buffered saline (0.1 mM, pH 7.4) or normal rabbit serum (isotype control) was used instead of primary antibody or ABC reagent as a negative control. Quantitative image analysis was done based on previous methods (Sanchez-Ramos et al. (2009)). Images were acquired using an Olympus BX60 microscope with an attached digital camera system (DP-70, Olympus, Tokyo, Japan), and the digital image was routed into a Windows PC for quantitative analysis using SimplePCI software (Compix Inc., Imaging Systems, Cranberry Township, Pa.). Images of five 5-µm sections (150 µm apart) through both anatomic regions of interest (hippocampus and entorhinal cortex) were captured from each animal, and a threshold optical density was obtained that discriminated staining from background. Each region of interest was manually edited to eliminate artifacts. For Aβ burden analysis, data are reported as percentage of immunolabeled area captured (positive pixels) relative to the full area captured (total pixels). To evaluate synaptophysin immunoreactivity, after the mode of all images was converted to gray scale, the average intensity of positive signals from each image was quantified in the CA1 and CA3 regions of hippocampus as a relative number from zero (white) to 255 (black). Each analysis was done by a single examiner blinded to sample identities (T.M.).

Behavioral Tasks. Each analysis was done by a single examiner (N.G.) blinded to sample identities, and statistical analyses were performed by a single examiner (M.R.) blinded to treatment group identities. The code was not broken until analyses were completed.

Radial Arm Water Maze. For the RAWM task of spatial working memory (Arendash et al. (2001); Ethell et al. (2006); Arendash et al. (2007)), an aluminum insert was placed into a 100 cm circular pool to create 6 radially-distributed swim arms emanating from a central circular swim area. An assortment of 2-D and 3-D visual cues surrounded the pool. The number of errors prior to locating which one of the 6 swim arms contained a submerged escape platform (9 cm diameter) was determined for 5 trials/day.

There was a 30-min time delay between the 4th trial (T4; final acquisition trial) and 5th trial (T5; memory retention trial). The platform location was changed daily to a different arm, with different start arms for each of the 5 trials semi-randomly selected from the remaining 5 swim arms. During each trial (60 s maximum), the mouse was returned to that trial's start arm upon swimming into an incorrect arm and the latency time required to locate the submerged platform was recorded. If the mouse did not find the platform within a 60-s trial, it was guided to the platform for a 30-s stay. The numbers of errors and escape latency during trials 4 and 5 are both considered indices of working memory and are temporally similar to standard registration/recall testing of specific items used clinically in evaluating AD patients.

Cognitive Interference Task. This task was designed to mimic, measure-for-measure, a cognitive interference task recently utilized clinically to discriminate between normal aged, MCI, and AD patients (Loewenstein et al. (2004)). The task involves two RAWM set-ups in two different rooms, with two sets of visual cues different from those utilized in standard RAWM testing. The task requires animals to remember a set of visual cues (in RAWM-A), so that following interference with a different set of cues (in RAWM-B), the initial set of cues can be recalled to successfully solve the RAWM task. Five behavioral measures were examined: A1-A3 (Composite three-trial recall score from first 3 trials performed in RAWM-A), B (proactive interference measure attained from a single trial in RAWM-B), A4 (retroactive interference measure attained during a single trial in RAWM-A), and A5 (delayed-recall measure attained from a single trial in RAWM-A following a 20-min delay between A4 and A5). As with the standard RAWM task, this interference task involves the platform location being changed daily to a different arm for both RAWM set-ups. For A1 and B trials, the animal is initially allowed one minute to find the platform on their own before being guided to the platform. Then the actual trial is performed in each case. As with the standard RAWM task, animals were given 60s to find the escape platform per trial, with the number of errors and escape latency recorded per trial.

Statistical Analysis. Statistical analysis of amyloid plaque parameters from ipsilateral GM-CSF administration versus contralateral aCSF-injection hemispheres was performed using paired Student t-test with a P-Value of <0.05 considered significant. For statistical analysis of RAWM data, the 8-days of pre-treatment testing (four 2-day blocks) or the 4-days of post-treatment testing (two 2-day blocks) were evaluated for individual blocks, as well as over all blocks, using one-way ANOVAs. Thereafter, post hoc pair-by-pair differences between groups were resolved with the Fisher LSD (least significant difference) test. For statistical analysis of cognitive interference data, both 2-day blocks were analyzed separately, as were all four days collectively. One way ANOVA's were employed for each of the four behavioral measures analyzed, followed by post hoc Fisher's LSD test to determine significant group differences at P<0.05. Statistical analysis of amyloid plaque deposition and synaptophysin staining from subcutaneous GM-CSF administration was performed using two-tailed homoscedastic Student t-test with a P value of <0.05 considered significant.

EXAMPLE 2

Alzheimer's disease is an age-related, progressive neurodegenerative disorder that presents as increasing decline in cognitive and executive function. Alzheimer dementia is associated with cerebrovascular dysfunction (Humpel and Marksteiner (2005)), extracellular accumulation of amyloid β (Aβ) peptides in the brain parenchyma and vasculature walls (Rhodin et al. (2000); Scheuner et al. (1996)) (predominantly $A\beta_{1-42}$ and $A\beta_{1-40}$), and intraneuronal accumulation of neurofibrillary tangles consisting of hyperphosphorylated Tau proteins (Rapoport et al. (2002)). Associated neuroinflammation may contribute to AD pathogenesis (Griffin et al. (1989); Akiyama et al. (2000); Wyss-Coray (2006)), as the inflammatory proteins apolipoprotein E (apoE) and α1-Antichymotrypsin (ACT) catalyze the polymerization of Aβ peptides into amyloid filaments in vivo and in vitro (Wisniewski et al. (1994); Ma et al. (1996); Potter et al. (2001); Nilsson et al. (2004); Padmanabhan et al. (2006)). However, NSAIDs have failed to reverse or prevent AD pathology, and dystrophic microglia are suggested to precede neurodegenerative dementia (Streit et al. (2009)). It has also been shown that amyloid plaques form rapidly and then become decorated by microglia (Koenigsknecht-Talboo et al. (2008); Meyer-Luehmann et al. (2008)), both resident and bone marrow-derived, suggesting an ability and intention to remove amyloid (Malm et al. (2005); Simard and Rivest (2004); Simard et al. (2006)).

Rheumatoid arthritis is an autoimmune disease in which inflamed synovial tissue and highly vascularized pannus forms, irreparably damaging the cartilage and bone. In this inflammatory pannus, leukocyte populations are greatly expanded, and many proinflammatory factors are produced that work together in feed-forward mechanisms, further increasing leukocytosis, cytokine/chemokine release, osteoclastogenesis, angiogenesis, and autoantibody production (rheumatoid factors and anti-citrullinated protein antibodies) (Szekanecz and Koch (2007); van der Voort et al. (2005); Schellekens et al. (2000)). Additionally, the adaptive immune system presents a Th17 phenotype within $CD4^+$ lymphocytes, with ultimate production of interleukin (IL-17) which is then responsible for inducing much of the pro-inflammatory effects (Parsonage et al. (2008); Cox et al. (2008)). Further enhancements of leukocyte populations come from local expression of colony-stimulating factors: M-CSF (macrophage), G-CSF (granulocyte), and GM-CSF (granulocyte-macrophage) (Seitz et al. (1994); Leizer et al. (1990); Nakamura et al. (2000)).

Although up-regulated leukocytes in RA could potentially enter into the brain and inhibit development of AD pathology and/or neuronal dysfunction, lymphocytic infiltrates into AD patient brains have not been reported. The lack of infiltration suggests that activation of the innate immune system might be responsible for preventing AD pathology in RA patients. For instance, complement proteins are up-regulated in AD brain, and inhibition of C3 convertase significantly increases amyloid pathology in AD mice (Wyss-Coray et al. (2002)). Bone marrow-derived microglia play a critical role in restricting amyloid deposition, but this association declines with age, while AD pathology increases (Simard et al. (2006)). El Khoury and colleagues have shown that microglia are actually protective against AD pathogenesis in multiple ways, i.e., through delay of amyloidosis via chemokine receptor (CCR2) recruitment, by up-regulation of its ligand, monocyte chemotactic protein-1 (MCP-1/CCL2), by induced expression of Aβ-binding scavenger receptors (CD36, scavenger receptor A, and receptor for advanced glycation end products), and by induced expression of Aβ-degrading enzymes [neprilysin, insulysin, and matrix metalloproteinase (MMP9)]. However, the expression of these receptors and enzymes also decreases with age (Hickman et al. (2008); El Khoury et al. (2007)).

To investigate the interplay of the innate immune system and AD, we studied the effects on AD pathology of the three structurally-unrelated colony-stimulating factors (M-CSF, G-CSF, and GM-CSF), which are all up-regulated in RA (Seitz et al. (1994); Leizer et al. (1990); Nakamura et al. (2000)). These CSFs enhance the survival of their respective leukocytes and drive their proliferation and differentiation from monocytic precursors. M-CSF and G-CSF induce specific subsets of the innate immune system, while GM-CSF induces the full range of innate cells. Using bilateral intracerebroventricular infusion of M-CSF for two weeks into PS/APP mice, we first examined M-CSF's effect on plaque deposition. Immunohistochemical analysis showed considerable variances of amyloid deposition between mice of similar age (FIG. 10), significantly compromising our ability to determine M-CSF's effect in a limited mouse cohort. While improving our drug delivery system by developing novel bilateral brain infusion catheters, we found that parenchymally-infused recombinant peptides remained localized to the infused hemisphere. These findings led us to administer the CSFs as a unilateral intrahippocampal bolus with a contralateral injection of vehicle as control, thus obviating the need for large numbers of transgenic mice and age-matched littermate controls to obtain statistical significance. Each CSF was stereotaxically injected into the hippocampus of 4 mice, with artificial cerebrospinal fluid vehicle (aCSF) injected contralaterally. The mice were sacrificed 7 days post-injection.

Figure 11A:
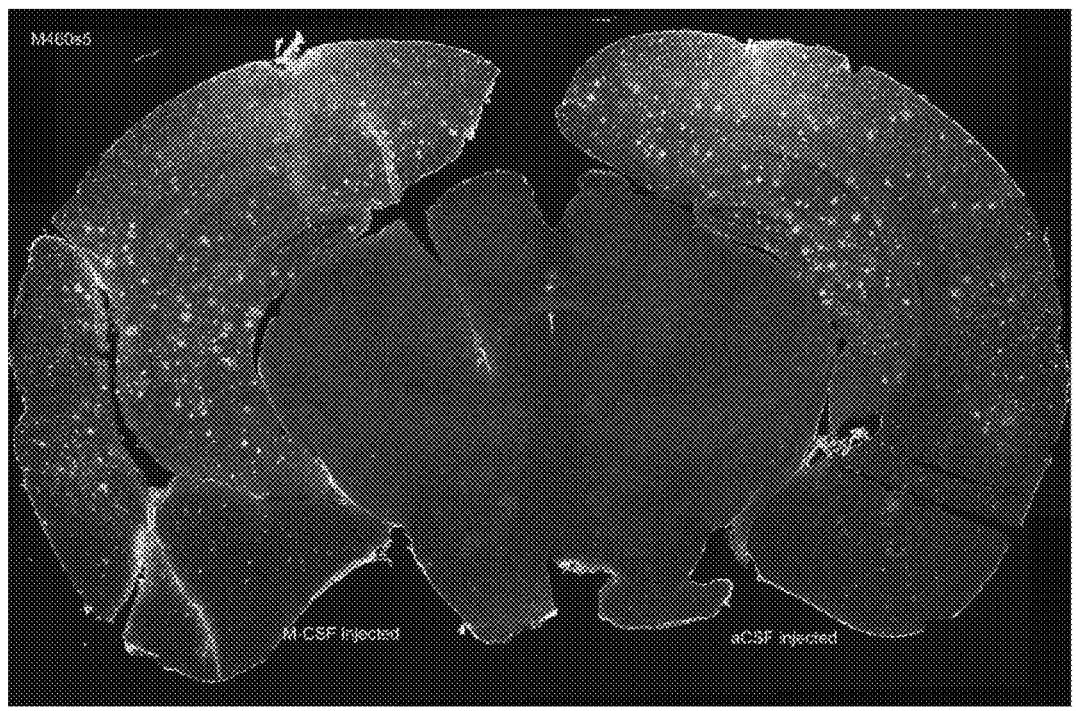
FIGS. 11A-11C show intrahippocampal injection of M-CSF (left hemisphere) and aCSF (right hemisphere).
Figure 11B:
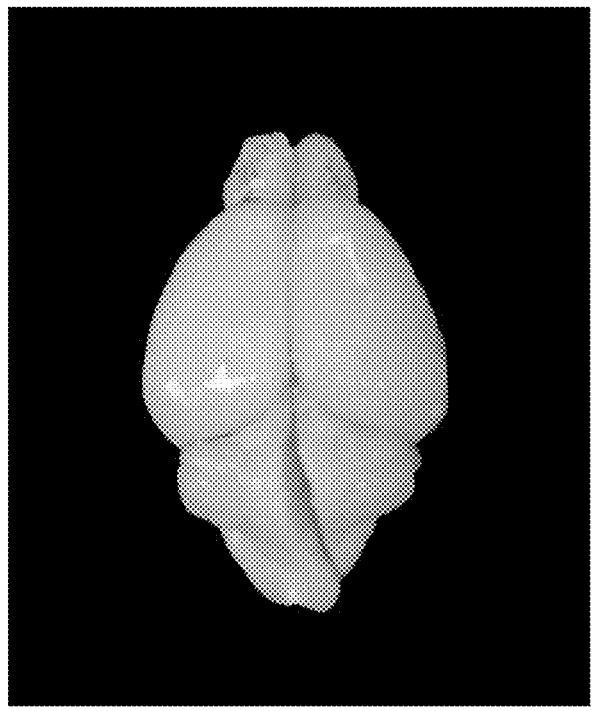
Figure 11C:
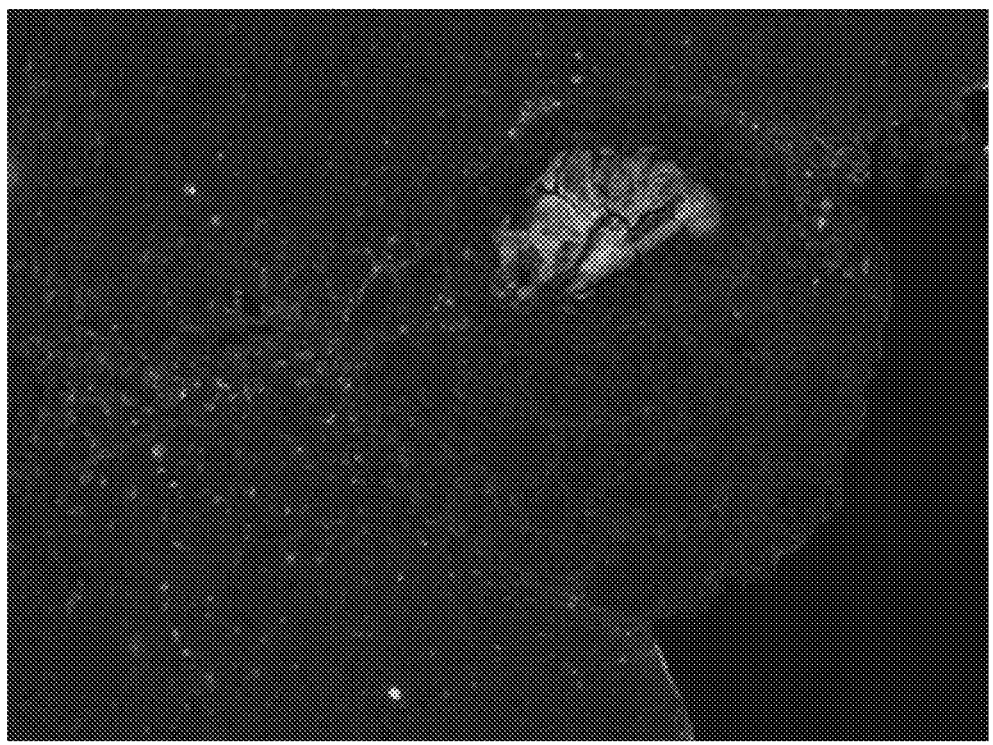

Remarkably, M-CSF injections resulted in visible swelling of the entire treated hemisphere, noticeable fragility on sectioning, and in one mouse, an apparent hyperplasia at the injection site (FIG. 11C). Overexpression of M-CSF and/or its receptor in mammary glands has similarly resulted in tumor formation and hyperplasia (Kirma et al. (2004)). Amyloid plaque loads were not significantly changed in the M-CSF-injected hemispheres as compared to the control sides (data not shown). However, Boissonneault et al. (2009) published that chronic intraperitoneal (i.p.) injection of M-CSF prevents and reverses amyloid deposition and cognitive impairment. Using GFP-expressing bone marrow, the authors also found that M-CSF induced a significant accumulation of bone marrow-derived microglia (Boissonneault et al. (2009)). Differences between these data and ours point to different study lengths and dosage effects, with Boissonneault et al. delivering chronic i.p. 1.3 µg M-CSF per injection, compared to our 5 µg intrahippocampal bolus.

Figure 12A:
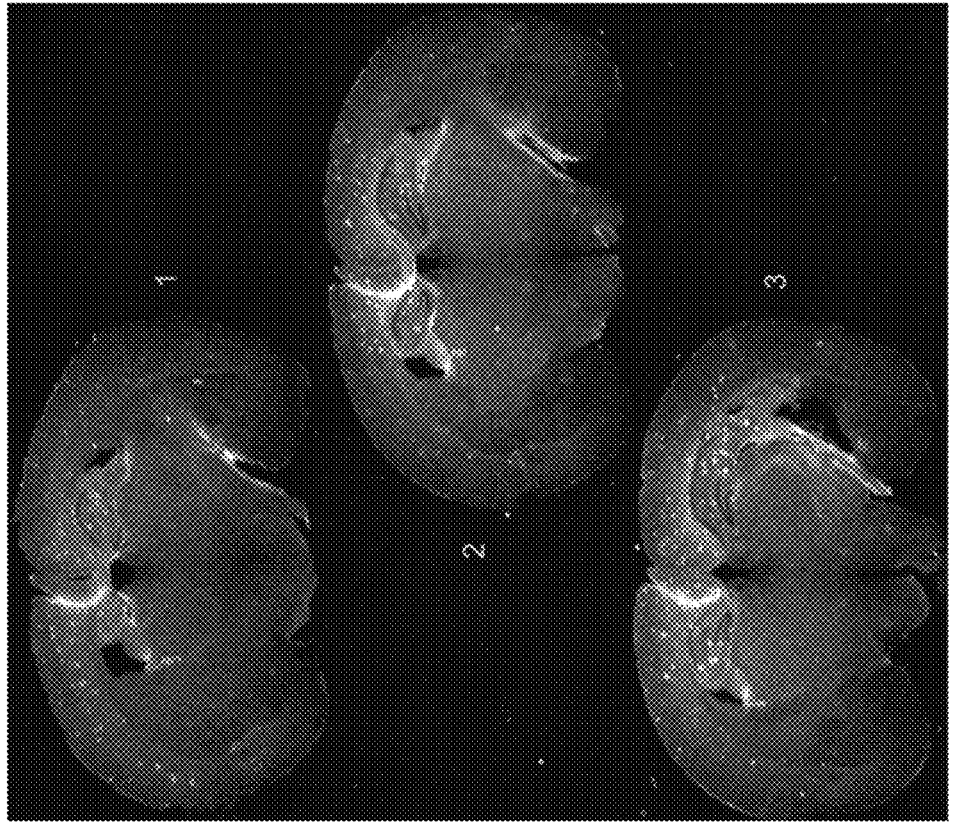
FIGS. 12A and 12B show intrahippocampal injection of G-CSF (left hemisphere) and aCSF (right hemisphere). Amyloid plaques indicated as white spots. Although the brain was sectioned at a slight angle, visual observation of amyloid plaques show a general reduction throughout the left G-CSF-injected hemisphere. Cryosectioned at 14 µm and stained with 6E10/IR800. Scanned on the Licor Odyssey and enlarged for visualization. Sections numbered 1 through 6 and correspond with anterior to posterior.
Figure 12B:
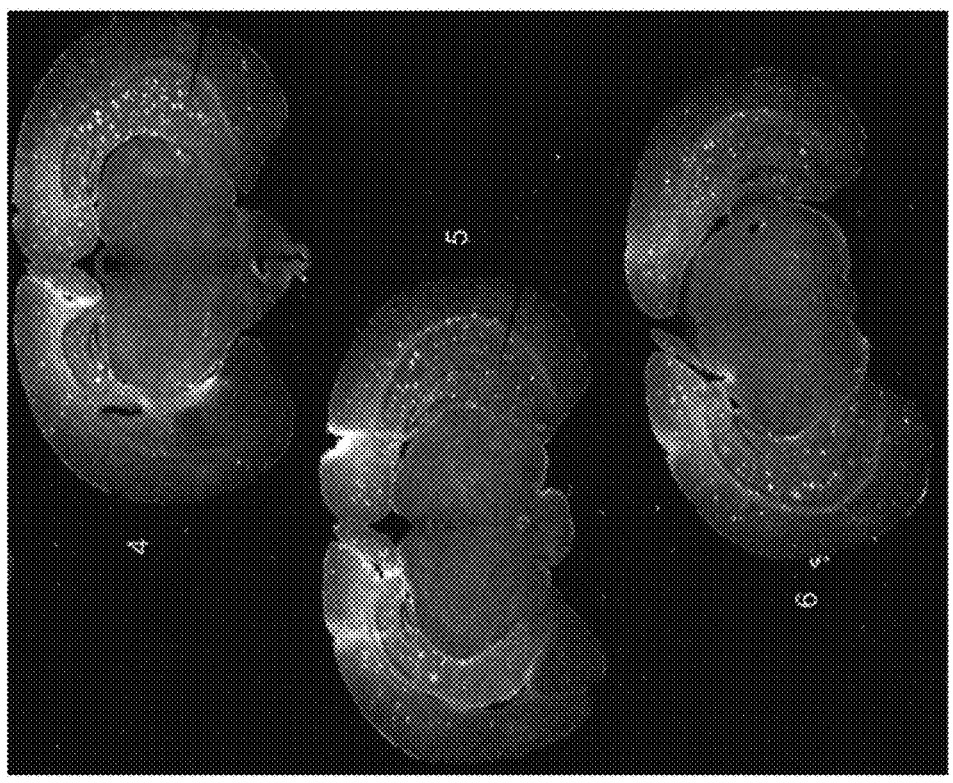
Figure 13A:
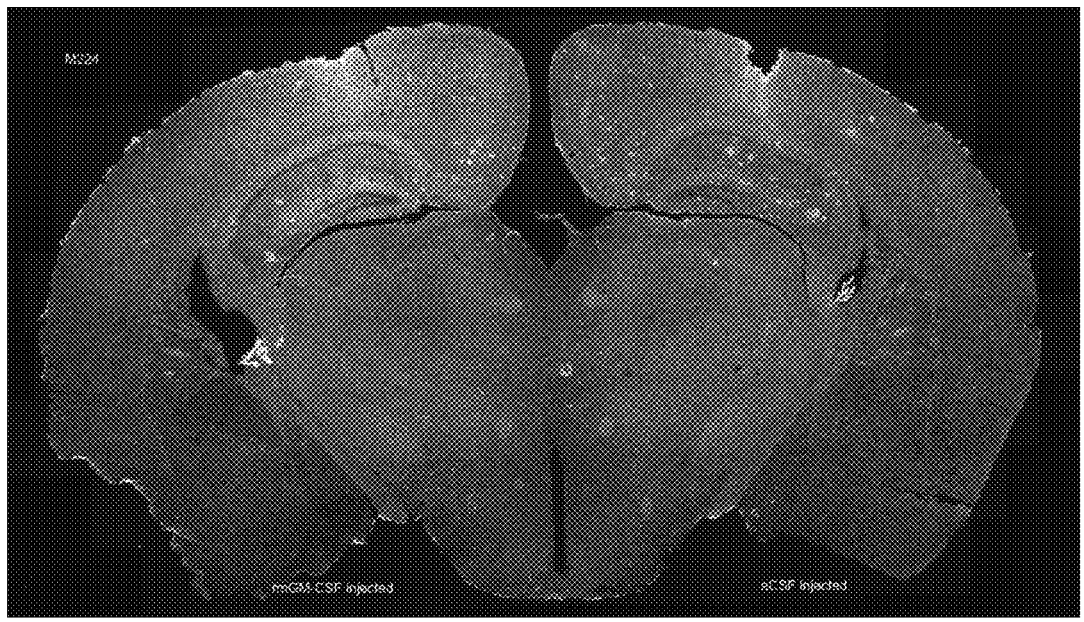
FIGS. 13A-13D show intrahippocampal injection of GM-CSF (left hemisphere) and aCSF (right hemisphere). Representative sections of each mouse proximal to injection site. Tissue sections stained with MabTech α-Aβ/Alexa 488. White spots indicate amyloid plaque immunolabelling. Images are montages of about 145 pictures taken at 10×.
Figure 13B:
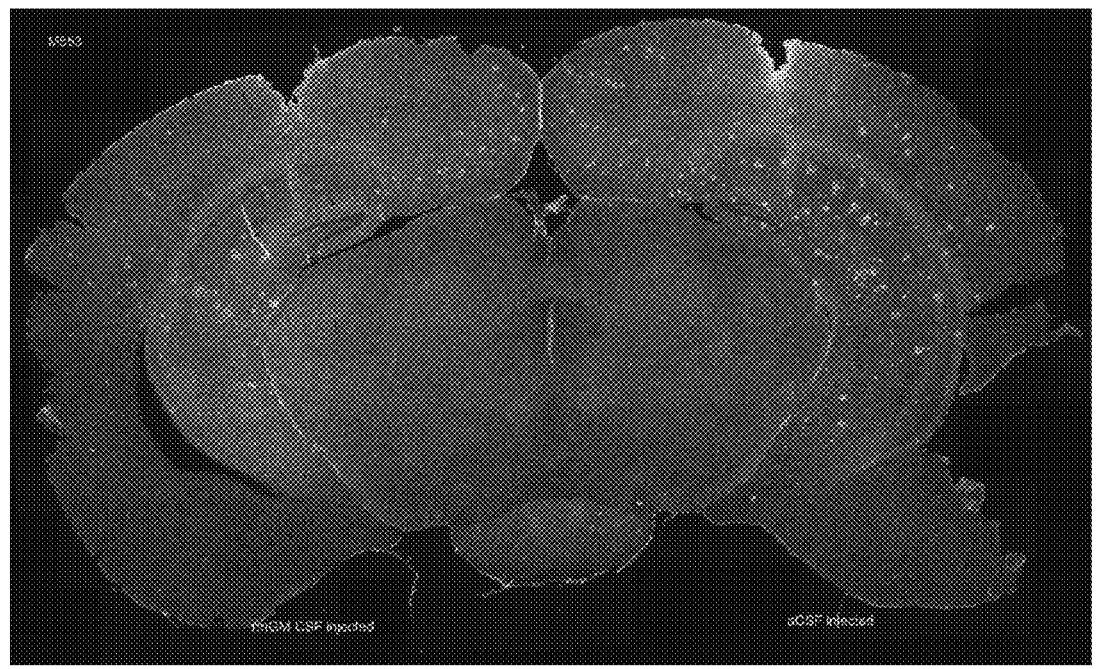
Figure 13C:
Figure 13D:
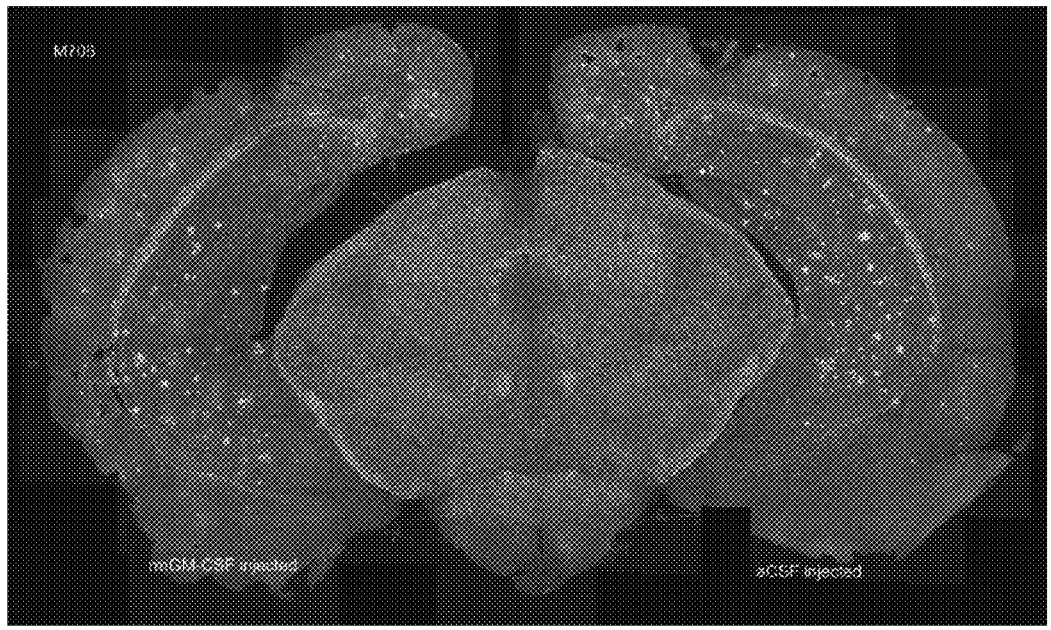
Figures 1, 14A:
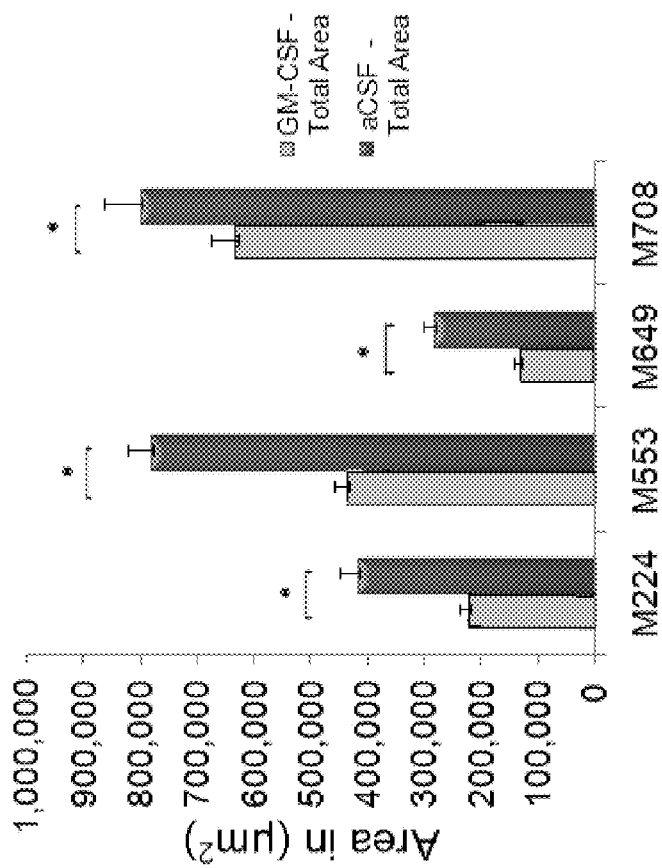
Figures 1, 14B:
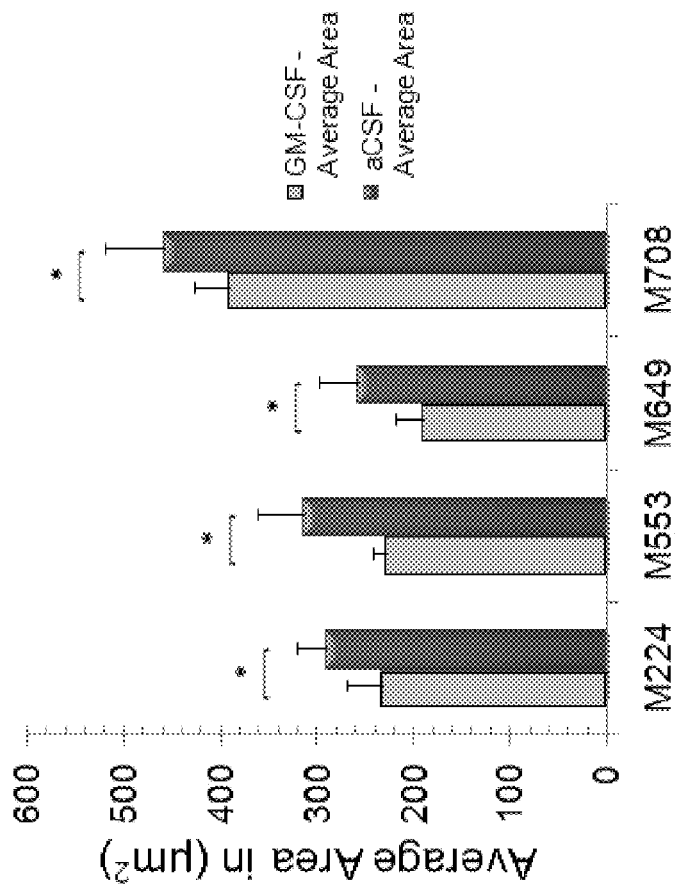
Figures 1, 14C:
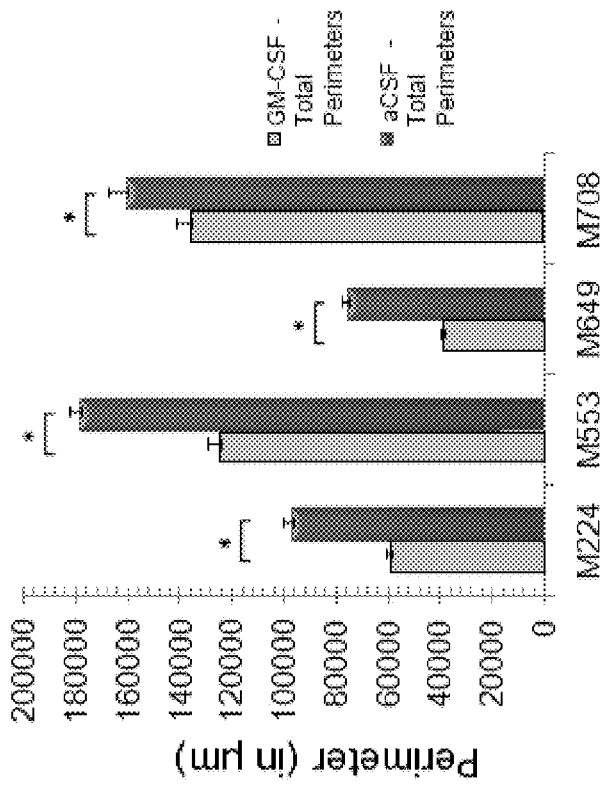
Figures 1, 14D:
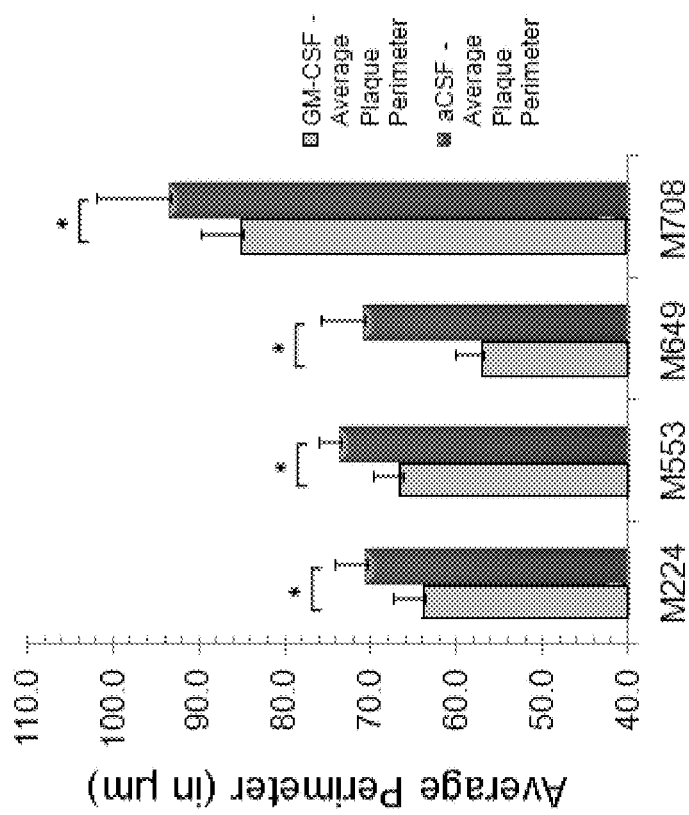
Figures 1, 14E:
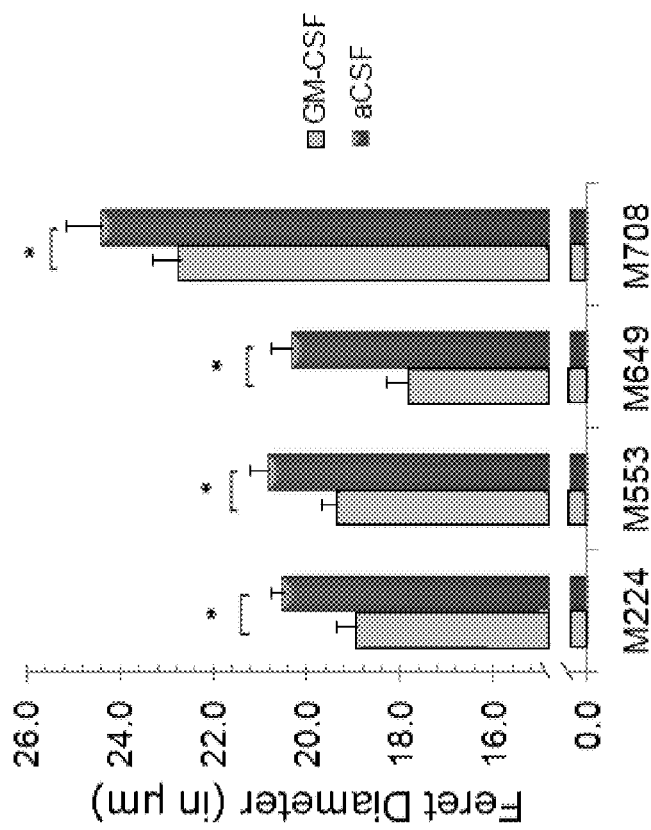
Figures 1, 14F:
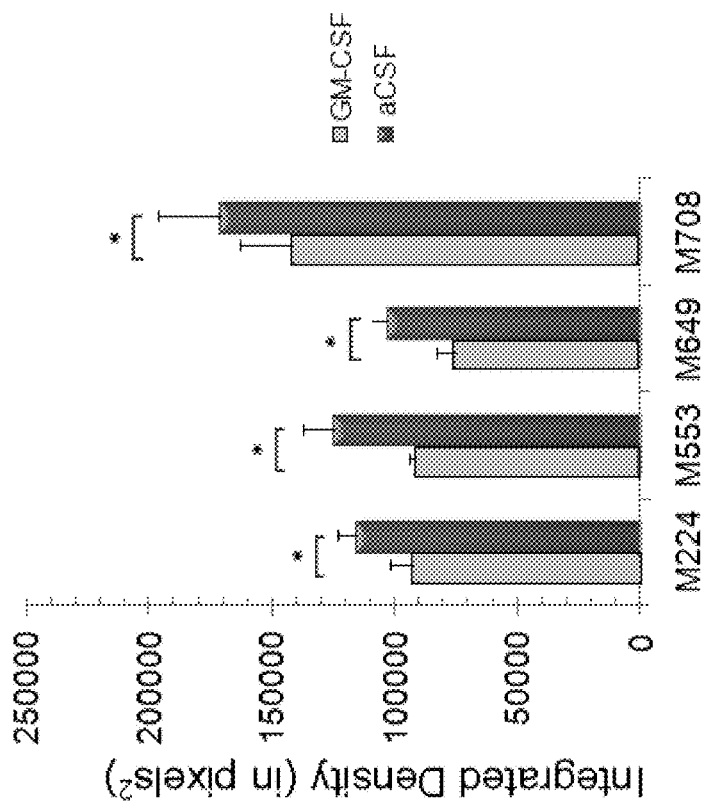

In contrast to M-CSF, G-CSF injections did not induce swelling and showed some modest reductions of amyloid deposition (FIGS. 12A and 12B), which was corroborated by independent observations by fellow investigators (Sanchez-Ramos et al. (2009)). However, GM-CSF injections resulted in pronounced amyloid reductions, as compared to control hemispheres (FIGS. 13A-13D), and therefore all our subsequent experiments focused on studying the effects of GM-CSF in AD mice. Quantification of amyloid plaques revealed significant reductions within individual mice and overall significant reductions for all plaque parameters measured (FIG. 6B and FIGS. 14A-14D-1). The feret diameter and the integrated density parameters were reduced throughout the GM-CSF-injected hemispheres of all 4 mice, indicating that the overall plaque sizes and dense cores were reduced simultaneously. The percent reduction in plaque deposition between individual sections of the same mouse and between different mice varied within a range of 8 to 62% (data not shown) and thereby further highlights the variance of amyloid depositions throughout each brain and between multiple mice.

Based upon these pathology data, we investigated the effect of subcutaneous GM-CSF injection on AD pathology and cognitive function. Prior to GM-CSF treatment, APPsw+PS1(Tg) mice were first confirmed by RAWM testing to be cognitively-impaired for working memory. Both the non-transgenic control mice (NT) and the Tg mice were then sub-divided into two cognitively-balanced groups, for either GM-CSF or saline treatment. RAWM testing post-injection re-confirmed that Tg control mice were substantially impaired compared to NT control mice. This impairment was evident in individual blocks of testing, but also over all 4 days of testing (FIGS. 7A-7D). In sharp contrast, GM-CSF-treated Tg mice performed equally well or better than NT control mice during individual blocks and overall. GM-CSF-treated NT mice performed as well as or slightly better than NT controls (FIGS. 7A-7D).

Before evaluation in the Cognitive Interference Task, the mice rested two days. This task mimics human interference testing, which distinguishes mild cognitive impairment (MCI) patients from aged controls with a high degree of accuracy (Loewenstein et al. (2004)). In all four cognitive interference measures assessed over 4 days of testing (FIG. 7E), Tg control mice were clearly impaired compared to NT mice, and Tg mice treated with GM-CSF exhibited significantly better 3-trial recall and delayed recall compared to Tg controls. Indeed, for all four cognitive measures, GM-CSF-treated transgenic AD mice performed similarly to NT mice. A particularly strong effect of GM-CSF treatment in Tg mice was evident for the proactive interference measure during the first half of testing (FIG. 7F), wherein GM-CSF-treated Tg mice performed substantially better than Tg controls and identically to both groups of NT mice. Susceptibility to proactive interference has been reported to be a more sensitive marker for differentiating MCI and AD patients from aged normals than traditional measures of delayed recall and rate of forgetting (Loewenstein et al. (2004)). Parenthetically, even the GM-CSF-treated NT mice showed a trend towards improved cognition in behavioral studies, albeit not statistically significant. Subsequent analysis of brains from Tg mice of this study revealed that GM-CSF treatment induced large reductions in amyloid burdens within entorhinal cortex ($\downarrow$55%) and hippocampal ($\downarrow$57%) compared to control Tg mice (FIG. 8E).

The improved cognitive function and reduced cortical amyloidosis of GM-CSF-treated Tg mice were paralleled by increased synaptophysin immunoreactivity in both CA1 and CA3 (FIGS. 9A-9E), indicating increased synaptic density in these hippocampal areas. Prior work has shown that adult neural stem cells in hippocampal dentate gyms (DG) express GM-CSF receptors, and GM-CSF increases neuronal differentiation of these cells in a dose-dependent fashion (Kruger et al. (2007)). Thus, one mechanism for the observed GM-CSF-induced cognitive improvement is enhanced removal of deposited A$\beta$ in hippocampus, with ensuing neuronal growth/synaptic differentiation of DG mossy fiber innervation to CA3, resulting in increased innervation/synaptogenesis of Schaffer collaterals into CA1. Removal of deposited A$\beta$ from entorhinal cortex may also increase perforant pathway viability to hippocampal projection fields in DG and CA1. Thus GM-CSF-induced enhancement of hippocampal/entorhinal cortex circuitry, critical for working (short-term) memory, may underlie GM-CSF's reversal of working memory impairment in Alzheimer's Tg mice.

EXAMPLE 3

Four 10-12 month old PS/APP mice were stereotaxically injected with 5 µg rmGM-CSF into the hippocampus in one hemisphere of the brain and with vehicle (aCSF: artificial cerebrospinal fluid) contralaterally. Mice were euthanized and saline-perfused 7 days later, fixed with 10% Formalin, and either cryosectioned at 14 µm or paraffin-embedded and sectioned at 5 µm. Standard immunohistochemical techniques used 6E10, and MabTech's anti-Aβ antibodies to label amyloid deposition. Microscopy and image processing were performed on a Zeiss ImagerZ1 using Axiovision software. ImageJ was utilized to quantify amyloid deposition.

Sixteen 10-12 month old PS/APP mice and sixteen non-transgenic age-matched controls were cognitively pretested by RAWM, a working memory paradigm. Eight mice from each group were semi-randomly chosen for sub-cutaneous injections (5 µg/day) of rmGM-CSF. The other half received daily injections of vehicle (saline). There was a 15 day rest period after pre-testing before daily injections began. Mice were injected for 10 days prior to 4 days of RAWM post-testing. There was a 2 day rest period before 6 days of Cognitive Interference task testing. Injections were given throughout testing and more than 1 hour before behavioral tests were performed. Behavioral testing and analysis were performed by separate staff, who were blinded to group identities.

Results:

Bolus intrahippocampal injection of rmGM-CSF reduced amyloid plaque deposition, throughout the respective brain hemispheres, by as much as 60%. In the rmGM-CSF sub-cutaneous injections, PS/APP mice, shown to be cognitively impaired compared to controls, significantly reversed their cognitive impairment in the standard RAWM task. In the Cognitive Interference task, the PS/APP mice that received rmGM-CSF showed similar results as that of the non-transgenic mice in all 4 cognitive measures. However, reductions in amyloid plaque deposition were not observed in the sub-cutaneous study.

GM-CSF significantly reverses Alzheimer's disease-like pathology and improves cognition in vivo.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,559,157
U.S. Pat. No. 4,608,392
U.S. Pat. No. 4,820,508
U.S. Pat. No. 4,938,949
U.S. Pat. No. 4,992,478
U.S. Pat. No. 5,034,322
U.S. Pat. No. 5,106,739
U.S. Pat. No. 5,167,649
U.S. Pat. No. 5,625,136
U.S. Pat. No. 6,960,648
U.S. Published Patent Application No. 20020035243
U.S. Published Patent Application No. 20020120100
U.S. Published Patent Application No. 20030032594
International Application No. PCT/US08/73974

Akiyama, H. et al. (2000) Inflammation and Alzheimer's disease. *Neurobiol Aging* 21, 383-421.

Altschul, S. F. et al. (1990) "Basic Local Alignment Search Tool" *J. Mol. Biol.* 215:403-410.

Altschul, S. F. et al. (1997) "Gapped BLAST and PSI-BLAST: A New Generation of Protein Database Search Programs" *Nucl. Acids Res.* 25:3389-3402.

Arendash, G W et al. (2001) "Progressive, age-related behavioral impairments in transgenic mice carrying both mutant amyloid precursor protein and presenilin-1 transgenes" *Brain Res* 891:42-53

Arendash, G W et al. (2007) "A diet high in omega-3 fatty acids does not improve or protect cognitive performance in Alzheimer's transgenic mice" *Neuroscience* 149:286-302

Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.

Boissonneault, V. et al. (2009) Powerful beneficial effects of macrophage colony-stimulating factor on beta-amyloid deposition and cognitive impairment in Alzheimer's disease. *Brain* 132, 1078-1092.

Bundgaard, H., Ed. (1985) Design of Prodrugs, Elsevier

Bundgard, H. (1992) *Advanced Drug Delivery Reviews*, 8:1-38

Cox, C. A. et al. (2008) Both Th1 and Th17 are immunopathogenic but differ in other key biological activities. *J Immunol* 180, 7414-7422.

de Boer, H. A., Comstock, L. J., Vasser, M. (1983) "The tac promoter: a functional hybrid derived from the trp and lac promoters" *Proc. Natl. Acad. Sci. USA* 80(1):21-25.

El Khoury, J. et al. (2007) Ccr2 deficiency impairs microglial accumulation and accelerates progression of Alzheimer-like disease. *Nat Med* 13, 432-438.

Ethell, D W et al. (2006) "Abeta-specific T-cells reverse cognitive decline and synaptic loss in Alzheimer's mice" *Neurobiol Dis* 23:351-361

Felgner, P. L., T. R. Gadek, M. Holm, R. Roman, H. W. Chan, M. Wenz, J. P. Northrop, G. M. Ringold, M. Danielsen (1987) "Lipofection: a highly efficient, lipid-mediated DNA-transfection procedure" *Proc Natl Acad Sci U. S.A.* 84(21):7413-7417.

Fisher, J. W. (2003) "Erythropoietin: physiology and pharmacology update" *Exp Biol Med* (Maywood), 228(1):1-14.

Götz, J, F. Chen, J. van Dorpe, R. M. Nitsch (2001) "Formation of neurofibrillary tangles in P3011 tau transgenic mice induced by Abeta 42 fibrils" *Science*, 293 (5534):1491-5.

Griffin, W. S. et al. (1989) Brain interleukin 1 and S-100 immunoreactivity are elevated in Down syndrome and Alzheimer disease. *Proc Natl Acad Sci USA* 86, 7611-7615.

Hickman, S. E., Allison, E. K. and El Khoury, J. (2008) Microglial dysfunction and defective beta-amyloid clearance pathways in aging Alzheimer's disease mice. *J Neurosci* 28, 8354-8360.

Higuchi, T. and Stella, V. (1987) "Pro-drugs as Novel Delivery Systems", 14 A. C.S. Symposium Series, and Bioreversible Carriers in Drug Design, E. B. Roche, Ed., American Pharmaceutical Association and Pergamon Press Humpel, C. and Marksteiner, J. (2005) Cerebrovascular damage as a cause for Alzheimer's disease. *Curr Neurovasc Res* 2, 341-347.

Karlin S., Altschul, S. F. (1990) "Methods for Assessing the Statistical Significance of Molecular Sequence Features by Using General Scoring Schemes" *Proc. Natl. Acad. Sci. USA* 87:2264-2268.

Karlin S., Altschul, S. F. (1993) "Applications and Statistics for Multiple High-Scoring Segments in Molecular Sequences" *Proc. Natl. Acad. Sci. USA* 90:5873-5877.

Kirma, N. et al. (2004) Overexpression of the colony-stimulating factor (CSF-1) and/or its receptor c-fms in mammary glands of transgenic mice results in hyperplasia and tumor formation. *Cancer Res* 64, 4162-4170.

Koenigsknecht-Talboo, J. et al. (2008) Rapid microglial response around amyloid pathology after systemic anti-Abeta antibody administration in PDAPP mice. *J Neurosci* 28, 14156-14164.

Krogsgaard-Larsen and Bandaged, H., Eds. (1991) A Textbook of Drug Design and Development, Chapter 5 "Design and Applications of Prodrugs" 113-191

Kruger, C., Laage, R., Pitzer, C., Schabitz, W. R. and Schneider, A. (2007) The hematopoietic factor G M-CSF (granulocyte-macrophage colony-stimulating factor) promotes neuronal differentiation of adult neural stem cells in vitro. *BMC Neurosci* 8, 88.

Leizer, T., Cebon, J., Layton, J. E. and Hamilton, J. A. (1990) Cytokine regulation of colony-stimulating factor production in cultured human synovial fibroblasts: I. Induction of G M-CSF and G-CSF production by interleukin-1 and tumor necrosis factor. *Blood* 76, 1989-1996.

Loewenstein, D. A. et al. (2004) Semantic interference deficits and the detection of mild Alzheimer's disease and mild cognitive impairment without dementia. *J Int Neuropsychol Soc* 10, 91-100.

Ma, J., Brewer, H. B., Jr. and Potter, H. (1996) Alzheimer A beta neurotoxicity: promotion by antichymotrypsin, ApoE4; inhibition by A beta-related peptides. *Neurobiol Aging* 17, 773-780.

Malm, T. M. et al. (2005) Bone-marrow-derived cells contribute to the recruitment of microglial cells in response to beta-amyloid deposition in APP/P S 1 double transgenic Alzheimer mice. *Neurobiol Dis* 18, 134-142.

Maniatis, T., Fritsch, E. F., Sambrook, J. (1982) *Molecular Cloning: A Laboratory Manual*, Cold Spring Harbor Laboratory, Cold Spring Harbor, N. Y.

Martin, B. K. et al. (2008) Cognitive function over time in the Alzheimer's Disease Anti-inflammatory Prevention Trial (ADAPT): results of a randomized, controlled trial of naproxen and celecoxib. *Arch Neurol* 65, 896-905.

McGeer, P. L., Rogers, J. and McGeer, E. G. (2006) Inflammation, anti-inflammatory agents and Alzheimer disease: the last 12 years. *J Alzheimers Dis* 9, 271-276.

Meyer-Luehmann, M. et al. (2008) Rapid appearance and local toxicity of amyloid-beta plaques in a mouse model of Alzheimer's disease. *Nature* 451, 720-724.

Nakamura, H. et al. (2000) High serum and synovial fluid granulocyte colony stimulating factor (G-CSF) concentrations in patients with rheumatoid arthritis. *Clin Exp Rheumatol* 18, 713-718.

Nakeya, N. et al. (1984) *Chem. Pharm. Bull.,* 32:692

Nielsenw, N. M. and Bundgaard, H. (1988) "Glycolamide esters as biolabile prodrugs of carboxylic acid agents: Synthesis, stability, bioconversion, and physicochemical properties" *J. Pharm. Sci.,* 77(4):285-298.

Nilsson, L. N. et al. (2004) Cognitive impairment in PDAPP mice depends on ApoE and ACT-catalyzed amyloid formation. *Neurobiol Aging* 25, 1153-1167.

Padmanabhan, J., Levy, M., Dickson, D. W. and Potter, H. (2006) Alpha1-antichymotrypsin, an inflammatory protein overexpressed in Alzheimer's disease brain, induces tau phosphorylation in neurons. *Brain* 129, 3020-3034.

Parsonage, G. et al. (2008) Prolonged, granulocyte-macrophage colony-stimulating factor-dependent, neutrophil survival following rheumatoid synovial fibroblast activation by IL-17 and TNFalpha. *Arthritis Res Ther* 10, R47.

Potter, H., Wefes, I. M. and Nilsson, L. N. (2001) The inflammation-induced pathological chaperones ACT and apo-E are necessary catalysts of Alzheimer amyloid formation. *Neurobiol Aging* 22, 923-930.

Rapoport, M., Dawson, H. N., Binder, L. I., Vitek, M. P. and Ferreira, A. (2002) Tau is essential to beta-amyloid-induced neurotoxicity. *Proc Natl Acad Sci USA* 99, 6364-6369.

Rhodin, J., Thomas, T., Bryant, M. and Sutton, E. T. (2000) Animal model of Alzheimer-like vascular pathology and inflammatory reaction. *Ann N Y Acad Sci* 903, 345-352.

Ritchie, K. and S. Lovestone (2002) "The dementias" *Lancet,* 360(9347):1759-66.

Sanchez-Ramos, J. et al. (2009) Granulocyte Colony Stimulating Factor (G-CSF) Decreases Brain Amyloid Burdenand Reverses Cognitive Impairment in Alzheimer's Mice. *Neuroscience.*

Schellekens, G. A. et al. (2000) The diagnostic properties of rheumatoid arthritis antibodies recognizing a cyclic citrullinated peptide. *Arthritis Rheum* 43, 155-163.

Scheuner, D. et al. (1996) Secreted amyloid beta-protein similar to that in the senile plaques of Alzheimer's disease is increased in vivo by the presenilin 1 and 2 and APP mutations linked to familial Alzheimer's disease. *Nat Med* 2, 864-870.

Seitz, M., Loetscher, P., Fey, M. F. and Tobler, A. (1994) Constitutive mRNA and protein production of macrophage colony-stimulating factor but not of other cytokines by synovial fibroblasts from rheumatoid arthritis and osteoarthritis patients. *Br J Rheumatol* 33, 613-619.

Simard, A. R. and Rivest, S. (2004) Bone marrow stem cells have the ability to populate the entire central nervous system into fully differentiated parenchymal microglia. *FASEB J* 18, 998-1000.

Simard, A. R., Soulet, D., Gowing, G., Julien, J. P. and Rivest, S. (2006) Bone marrow-derived microglia play a critical role in restricting senile plaque formation in Alzheimer's disease. *Neuron* 49, 489-502.

Streit, W. J., Braak, H., Xue, Q. S. and Bechmann, I. (2009) Dystrophic (senescent) rather than activated microglial cells are associated with tau pathology and likely precede neurodegeneration in Alzheimer's disease. *Acta Neuropathol.*

Szekanecz, Z. and Koch, A. E. (2007) Macrophages and their products in rheumatoid arthritis. *Curr Opin Rheumatol* 19, 289-295.

van der Voort, R. et al. (2005) Elevated CXCL16 expression by synovial macrophages recruits memory T cells into rheumatoid joints. *Arthritis Rheum* 52, 1381-1391.

Widder, K. et al, Eds. (1985) Methods in Enzymology, Academic Press, 42:309-396

Wisniewski, T., Castano, E. M., Golabek, A., Vogel, T. and Frangione, B. (1994) Acceleration of Alzheimer's fibril formation by apolipoprotein E in vitro. *Am J Pathol* 145, 1030-1035.

Wyss-Coray, T. (2006) Inflammation in Alzheimer disease: driving force, bystander or beneficial response? *Nat Med* 12, 1005-1015.

Wyss-Coray, T. et al. (2002) Prominent neurodegeneration and increased plaque formation in complement-inhibited Alzheimer's mice. *Proc Natl Acad Sci USA* 99, 10837-10842.

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.

Fisher, J. W. (2003) "Erythropoietin: physiology and pharmacology update" *Exp Biol Med* (Maywood), 228:1-14).

Rogers, J. et al. (2006) "Peripheral clearance of amyloid beta peptide by complement C3-dependent adherence to erythrocytes" *Neurobiol Aging,* 27:1733-1739.

Cadman, E. D. and Puttfarcken, P. S. (1997) "Beta-amyloid peptides initiate the complement cascade without producing a comparable effect on the terminal pathway in vitro" *Exp Neurol* 146:388-394.

Helmy, K. Y. et al. (2006) "CRIg: a macrophage complement receptor required for phagocytosis of circulating pathogens" *Cell* 124:915-927.

Czygier, M., Lawicki, S., Stankiewicz, I. & Szmitkowski, M. (2007) [Stem cell factor (SCF) in the plasma and phagocytic functions of granulocytes in breast cancer patients]. *Przegl Lek* 64:1014-1017.

or animal relative to the level of Aβ peptide in the brain of the person or animal prior to administration of the GM-CSF or analog thereof.

2. The method of claim 1, wherein the GM-CSF is administered intracranially.

3. The method of claim 1, wherein the GM-CSF is administered by intracranial infusion.

4. The method of claim 1, wherein the GM-CSF is administered by subcutaneous, intradermal, intravenous, intramuscular, intraperitoneal, or intrasternal injection.

5. The method of claim 1, wherein the GM-CSF is administered to a non-neural cell or tissue.

6. The method of claim 1, wherein said method further comprises evaluating the person or animal for cognitive impairment prior to treatment.

7. The method of claim 1, wherein the GM-CSF is administered as a composition.

8. The method of claim 7, wherein the composition comprises a physiologically or pharmaceutically acceptable carrier, diluent, or solute.

9. The method of claim 1, wherein the Aβ peptide is a peptide designated as Aβpeptide 1-37, Aβ peptide 1-38, Aβ peptide 1-39, Aβ peptide 1-40, Aβ peptide 1-42, Aβ peptide 11-40, or Aβ peptide 11-42.

---

---

We claim:

1. A method for treating cognitive impairment associated with pathological amyloid beta (Aβ) peptide accumulation in the brain of a person or animal comprising administering to the person or animal an effective amount of a granulocyte/macrophage colony-stimulating factor (GM-CSF) or an analog thereof, wherein the analog is sargramostim, and wherein the level of an Aβ peptide is reduced in the person 10. The method of claim 1, wherein the GM-CSF is administered continuously to the person or animal over a period of time.

11. The method of claim 1, wherein the GM-CSF is administered at distinct intervals to the person or animal over a period of time.

12. The method of claim 1, wherein the GM-C SF is human GM-CSF.

13. The method of claim 1, wherein the Aβ peptide is present as an extracellular amyloid plaque.

14. The method of claim 1, wherein said method further comprises evaluating the person or animal for cognition prior to treatment.

15. The method of claim 1, wherein the GM-CSF comprises the amino acid sequence of SEQ ID NO:1, or the GM-CSF has greater than 95% sequence identity with the amino acid sequence of SEQ ID NO:1.

* * * * *

UNITED STATES PATENT AND TRADEMARK OFFICE
CERTIFICATE OF CORRECTION

PATENT NO. : 9,682,124 B2
APPLICATION NO. : 14/145303
DATED : June 20, 2017
INVENTOR(S) : Huntington Potter et al.

Page 1 of 1

It is certified that error appears in the above-identified patent and that said Letters Patent is hereby corrected as shown below:

Column 4,
Line 55, "a-trial" should read --3-trial--.

Column 32,
Line 32, "the tip" should read --the trp--.
Line 46, "(Maywood)" should read --*(Maywood)*--.
Line 61, "A. C.S. Symposium" should read --A.C.S. Symposium--.

Column 33,
Line 20, "factor G M-CSF" should read --factor GM-CSF--.
Line 27, "of G M-CSF" should read --of GM-CSF--.
Line 39, "APP/P S 1" should read --APP/PS1--.

Column 35,
Line 10, "(Maywood)" should read --*(Maywood)*--.

Column 36,
Line 22, "Aβpeptide" should read --Aβ peptide--.

Signed and Sealed this
Fourth Day of September, 2018

Andrei Iancu
*Director of the United States Patent and Trademark Office*